United States Patent
Tabuteau

(10) Patent No.: US 9,375,429 B2
(45) Date of Patent: *Jun. 28, 2016

(54) COMPOSITIONS AND METHODS COMPRISING ERYTHROHYDROXYBUPROPION AND RELATED COMPOUNDS FOR IMPROVING THE EFFICACY OF DEXTROMETHORPHAN

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/879,002

(22) Filed: Oct. 8, 2015

(65) Prior Publication Data

US 2016/0030421 A1  Feb. 4, 2016

Related U.S. Application Data

(63) Continuation of application No. 14/554,988, filed on Nov. 26, 2014, now Pat. No. 9,205,083, which is a continuation of application No. 14/550,618, filed on Nov. 21, 2014, now Pat. No. 9,198,905, which is a continuation-in-part of application No. PCT/US2014/064184, filed on Nov. 5, 2014.

(60) Provisional application No. 61/900,354, filed on Nov. 5, 2013.

(51) Int. Cl.
    *A61K 31/137* (2006.01)
    *A61K 31/485* (2006.01)
    *A61K 31/4748* (2006.01)

(52) U.S. Cl.
    CPC ............. *A61K 31/485* (2013.01); *A61K 31/137* (2013.01); *A61K 31/4748* (2013.01)

(58) Field of Classification Search
    None
    See application file for complete search history.

(56) References Cited

U.S. PATENT DOCUMENTS

| | | | |
|---|---|---|---|
| 2,676,177 A | 4/1954 | Schnider | |
| 3,819,706 A | 6/1974 | Mehta | |
| 4,687,660 A | 8/1987 | Baker et al. | |
| 5,166,207 A | 11/1992 | Smith | |
| 5,206,248 A | 4/1993 | Smith | |
| 5,350,756 A | 9/1994 | Smith | |
| 6,034,091 A | 3/2000 | Dante | |
| 6,197,830 B1 | 3/2001 | Frome | |
| 6,207,674 B1 | 3/2001 | Smith | |
| 6,333,332 B1 | 12/2001 | Han et al. | |
| 6,436,938 B1 | 8/2002 | Howard, Jr. | |
| 6,562,835 B1 | 5/2003 | Caruso | |
| 6,608,073 B1 | 8/2003 | Hussain et al. | |
| 6,780,871 B2 | 8/2004 | Glick et al. | |
| 6,897,241 B2 | 5/2005 | Frome | |
| 7,569,610 B2 | 8/2009 | Oberegger et al. | |
| 7,569,611 B2 | 8/2009 | Oberegger et al. | |
| 7,579,380 B2 | 8/2009 | Oberegger et al. | |
| 7,659,282 B2 | 2/2010 | Yakatan et al. | |
| 7,674,479 B2 | 3/2010 | Zerbe et al. | |
| 7,884,136 B2 | 2/2011 | Oberegger et al. | |
| 7,973,043 B2 | 7/2011 | Migaly | |
| 7,973,049 B2 | 7/2011 | Tung | |
| 8,017,623 B2 | 9/2011 | Singh | |
| 8,188,110 B2 | 5/2012 | Tung | |
| 8,227,484 B2 | 7/2012 | Yakatan et al. | |
| 8,461,102 B2 | 6/2013 | Royster, Jr. | |
| 8,541,436 B2 | 9/2013 | Tung | |
| 8,569,328 B1 | 10/2013 | Tabuteau | |
| 8,728,528 B2 | 5/2014 | Biggs et al. | |
| 8,796,302 B2 | 8/2014 | Hong et al. | |
| 8,932,628 B2 | 1/2015 | Oberegger et al. | |
| 9,168,234 B2 | 10/2015 | Tabuteau | |
| 9,198,905 B2 | 12/2015 | Tabuteau | |
| 9,205,083 B2 | 12/2015 | Tabuteau | |
| 9,238,032 B2 | 1/2016 | Tabuteau | |
| 9,278,095 B2 | 3/2016 | Tabuteau | |
| 2002/0004078 A1 | 1/2002 | Gelber et al. | |
| 2002/0103109 A1 | 8/2002 | Glick | |
| 2004/0092511 A1 | 5/2004 | Billstein et al. | |
| 2005/0085463 A1 | 4/2005 | Weiner et al. | |
| 2005/0203125 A1 | 9/2005 | Yakatan et al. | |

(Continued)

FOREIGN PATENT DOCUMENTS

| EP | 1224930 | 7/2002 |
|---|---|---|
| EP | 2397158 | 12/2011 |

(Continued)

OTHER PUBLICATIONS

Applicant's remark of case U.S. Appl. No. 14/604,397, filed Jul. 1, 2015.*
Chyka et al, Dextromethorphan poisoning: An evidence-based consensus guideline for out-of-hospital management, Clinical Toxicology 45: 662-667, 2007.
Fairstein, Moran et al., Regional-Dependent Intestinal Permeability and BCS Classification: Elucidation of pH-Related Complexity in Rats Using Pseudoephedrine, AAPS Journal, vol. 15, No. 2, pp. 589-597, Apr. 2013.
Gilron et al, A randomized, controlled trial of high-dose dextromethorphan in facial neuralgias, Neurology, 55: 964-971, Oct. (1 of 2). 2000.
Guzey et al, Change From the CYP2D6 Extensive Metabolizer to the Poor Metabolizer Phenotype During Treatment With Bupropion, Therapeutic Drug Monitoring, 24: 436-437, 2002.

(Continued)

*Primary Examiner* — Bong-Sook Baek
(74) *Attorney, Agent, or Firm* — K&L Gates LLP; Brent A. Johnson; Louis C. Cullman

(57) ABSTRACT

This disclosure relates to methods of improving the efficacy of dextromethorphan, or providing beneficial pharmacokinetic effects to dextromethorphan, comprising co-administering erythrohydroxybupropion, or a prodrug thereof, and dextromethorphan to a human being. Dosage forms, drug delivery systems, and methods related to dextromethorphan and erythrohydroxybupropion or a prodrug of erythrohydroxybupropion are also disclosed.

27 Claims, 11 Drawing Sheets

(56) References Cited

U.S. PATENT DOCUMENTS

| | | |
|---|---|---|
| 2005/0209218 A1 | 9/2005 | Meyerson et al. |
| 2005/0250767 A1 | 11/2005 | Weiner et al. |
| 2006/0258721 A1 | 11/2006 | Maddaford et al. |
| 2007/0042969 A1 | 2/2007 | Rauschkolb-Loffler et al. |
| 2008/0008748 A1 | 1/2008 | Beyreuther et al. |
| 2008/0081072 A1 | 4/2008 | Cherukuri |
| 2008/0286344 A1 | 11/2008 | Darmuzey et al. |
| 2009/0124583 A1 | 5/2009 | Nelson et al. |
| 2009/0162421 A1 | 6/2009 | Geisslinger et al. |
| 2009/0191257 A1 | 7/2009 | Smith |
| 2010/0029665 A1 | 2/2010 | Meyerson et al. |
| 2011/0039875 A1 | 2/2011 | Singh |
| 2011/0217371 A1 | 9/2011 | Shin et al. |
| 2011/0245208 A1 | 10/2011 | Diatchenko et al. |
| 2012/0053169 A1 | 3/2012 | Thomas |
| 2012/0083487 A1 | 4/2012 | Thomas |
| 2012/0252833 A1 | 10/2012 | Wertz et al. |
| 2013/0137714 A1 | 5/2013 | Berg |
| 2014/0162965 A1 | 6/2014 | Maggio |
| 2015/0087669 A1 | 3/2015 | Lammert et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2016/0008352 A1 | 1/2016 | Tabuteau |
| 2016/0030420 A1 | 2/2016 | Tabuteau |
| 2016/0030421 A1 | 2/2016 | Tabuteau |

FOREIGN PATENT DOCUMENTS

| | | |
|---|---|---|
| WO | WO98/50044 | 11/1998 |
| WO | WO00/41684 | 7/2000 |
| WO | WO00/59486 | 10/2000 |
| WO | WO2004075832 | 9/2004 |
| WO | WO2006092691 | 9/2006 |
| WO | WO2009006194 | 1/2009 |
| WO | WO2009011412 | 1/2009 |
| WO | WO2009062318 | 5/2009 |
| WO | WO2009062319 | 5/2009 |
| WO | WO2010000073 | 1/2010 |
| WO | WO2010062690 | 6/2010 |
| WO | WO2010062692 | 6/2010 |
| WO | WO2012118562 | 9/2012 |
| WO | WO2012118563 | 9/2012 |
| WO | WO2013136078 | 9/2013 |
| WO | WO2013158680 | 10/2013 |
| WO | WO2014100501 | 6/2014 |

OTHER PUBLICATIONS

ISR and Written Opinion for PCT/US2014/064184, mailed Mar. 12, 2015.
Kelly et al, The utility of the combination of dextromethorphan and quinidine in the treatment of bipolar II and bipolar NOS, Journal of Affective Disorders, 167: 333-335, 2014.
Kiptoo et al., Transdermal delivery of bupropion and its active metabolite, hydroxybupropion: a prodrug strategy as an alternative approach. J Pharm Sci. Feb. 2009; 98(2): 583-594.
Kotlyar et al, Inhibition of CYP2D6 Activity by Bupropion, Journal of Clinical Psychopharmacology, 25(2): 226-229, Jun. 2005.
Lauterbach, Edward C., Dextromethorphan as a potential rapid-acting antidepressant, Medical Hypotheses, 76(5): 717-719, 2011.
Lauterbach, Edward C.,An extension of hypotheses regarding rapid-acting, treatment-refractory, and conventional antidepressant activity of dextromethorphan and dextrorphan, Medical Hypotheses, 78(6): 693-702, 2012.
Lee et al, The DRD2/ANKK1 gene is associated with response to add-on dextromethorphan treatment in bipolar disorder, Journal of Affective Disorders, 138: 295-300, 2012.
Nelson et al, High-dose oral dextromethorphan versus placebo in painful diabetic neuropathy and postherpetic neuralgia, American Academy of Neurology, 48: 1212-1218. May 1997.
Nguyen et al, Involvement of Sigma-1 Receptors in the Antidepressant-like Effects of Dextromethorphan, PLOS One, 9(2). Feb. 1-9, 2014.
Pioro EP, et al., Dextromethorphan Plus Ultra Low-Dose Quinidine Reduces Pseudobulbar Affect, Ann Neurol. 2010; 68:693-702.
Pope et al., Pharmacokinetics of Dextromethorphan after Single or Multiple Dosing in Combination with Quinidine in Extensive and Poor Metabolizers, The Journal of Clinical Pharmacology, 44(10):1132-1142, 2004.
Reese et al, An in Vitro Mechanistic Study to Elucidate the Desipramine/Bupropion Clinical Drug-Drug Interaction, Drug Metabolism and Disposition, 36: 1198-1201, 2008.
Sang et al, Dextromethorphan and Memantine in Painful Diabetic Neuropathy and Postherpetic Neuralgia, Anesthesiology 96:1053-1061, 2002.
Semenchuk et al, Double-blind, randomized trial of bupropion SR for the treatment of neuropathic pain, Neurology 57:1583-1588, 2001.
Shah et al, Bupropion for the Treatment of Neuropathic Pain, American Journal of Hospice and Palliative Medicine, 27(5): 333-336, 2010.
Shaibani et al, Efficacy and Safety of Dextromethorphan/Quinidine at Two Dosage Levels for Diabetic Neuropathic Pain: A Double-Blind, Placebo-Controlled, Multicenter Study, Pain Medicine, 13: 243-254, 2012.
Silverstone PH, Williams R, McMahon L, Fleming R, Fogarty S. Convulsive liability of bupropion hydrochloride metabolites in Swiss albino mice. Annals of general psychiatry. 2008; 7:19.
Smith, Richard Alan, Dextromethorphan/quinidine: a novel dextromethorphan product for the treatment of emotional lability, Expert Opin., Pharmacother. 7(18):2581-2598, 2006.
Spina, Edoardo, Clinically Relevant Pharmacokinetic Drug Interactions with Second-Generation Generation Antidepressants: An Update, Clinical Therapeutics. 30(7):1206-1227, 2008.
Thisted et al, Dextromethorphan and Quinidine in Adult Patients with Uncontrolled Painful Diabetic Peripheral Neuropathy: A 29-Day, Multicenter, Open-Label, Dose-Escalation Study, Clinical Therapeutics, 28(10): 1607-1618, 2006.
Tod et al., Quantitative Prediction of Cytochrome P450 (CYP) 2D6-Mediated Drug Interactions, Clin Pharmacokinet 2011; 50 (8):519-530.
U.S. Appl. No. 14/550,618, filed Nov. 21, 2014 First Named Inventor: Herriot Tabuteau Assignee: Antecip Bioventures II LLC.
U.S. Appl. No. 14/554,947, filed Nov. 26, 2014 First Named Inventor: Herriot Tabuteau Assignee: Antecip Bioventures II LLC.
U.S. Appl. No. 14/554,988, filed Nov. 26, 2014 First Named Inventor: Herriot Tabuteau Assignee: Antecip Bioventures II LLC.
U.S. Appl. No. 14/555,085, filed Nov. 26, 2014 First Named Inventor: Herriot Tabuteau Assignee: Antecip Bioventures II LLC.
U.S. Appl. No. 14/602,177, filed Jan. 21, 2015 First Named Inventor: Herriot Tabuteau Assignee: Antecip Bioventures II LLC.
U.S. Appl. No. 14/604,397, filed Jan. 23, 2015 First Named Inventor: Herriot Tabuteau Assignee: Antecip Bioventures II LLC.
U.S. Appl. No. 14/617,624, filed Feb. 9, 2015 First Named Inventor: Herriot Tabuteau Assignee: Antecip Bioventures II LLC.
U.S. Appl. No. 14/628,062, filed Feb. 20, 2015 First Named Inventor: Herriot Tabuteau Assignee: Antecip Bioventures II LLC.
Weinbroum et al., The role of dextromethorphan in pain control, Canadian Journal of Anesthesia, 47(6): 585-596, 2000.
Wellbutrin label, GlaxoSmithKline, 2009.
Zhu, Andy Z.X. et al., *CYP2B6 and bupropion's smoking cessation pharmacology: the role of hydroxybupropion*, NIH Public Access Author Manuscript at p. 5, published in final edited form in 92(6) Clin. Pharmacol. Ther. 771 (Dec. 2012).
Zyban prescribing information updated Aug. 2014.
Abdel-Rahman et al., Potent Inhibition of Cytochrome P-450 2D6-mediated Dextromethorphan O-Demethylation by Terbinafine, Drug Metabolism and Disposition, 27(7), 770-775, Jul. 1999.
Bachmann, K., Chapter 12—Drug-drug interactions with an emphasis on drug metabolism and transport, Pharmacology Principles and Practice, Academic Press, 303-325, 2009.

(56) References Cited

OTHER PUBLICATIONS

Desmeules et al., Contribution of Cytochrome P-4502D6 Phenotype to the Neuromodulatory Effects of Dextromethorphan, Journal of Pharmacology and Experimental Therapeutics, 288(2), 607-612, Feb. 1999.

Dextromethorphan Product Labeling Under the OTC Monograph 21 CFR 341.74, 1 pg., last accessed Nov. 2013.

Droll et al., Comparison of Three CYP2D6 Probe Substrates and Genotype in Ghanaians, Chinese and Caucasians, Pharmacogenetics and Genomics, 8(4), 325-333, Aug. 1998.

Drug Interactions between Dextromethorphan/Guaifenesin and Wellbutrin XL®, Drugs.com, last accessed Apr. 11, 2016, 1 pg., available at: http://www.drugs.com/drug-interactions/dextromethorphan-guaifenesin-with-wellbutrin-xl-846-0-440-2469.html.

Garnock-Jones, Dextromethorphan/Quinidine: In Pseudobulbar Affect, CNS Drugs, 25(5), 435-45, May 2011.

GlaxoSmithKline, Zyban® Prescribing Information, Aug. 2011, 28 pgs, available at: http://www.accessdata.fda.gov/drugsatfda_docs/label/2011/020711s026lbl.pdf.

Howard et al., The Efficacy and Toxicity of Bupropion in the Elderly, Jefferson Journal of Psychiatry, 15(1), 34-38, Jan. 2000.

Humanwell PUR ACAP Pharmaceutical (Wuhan), Ltd., Dextromethorphan HBR, Prescribing information, 4 pgs., revised Jan. 2014.

Mizoguchi et al., Efficacy of a Single Evening Dose of Syrup containing Paracetamol, Dextromethorophan Hydrobromide, Doxylamine Succinate and Ephedrine Sulfate in Subjects with Multiple Common Cold Symptoms, International Journal of Clinical Pharmacology and Therapeutics, 45(4), 230-236, Apr. 2007.

Nakashima et al., Effect of Cinacalcet Hydrochloride, a New Calcimimetic Agent, on the Pharmacokinetics of Dextromethorphan: In Vitro and Clinical Studies, The Journal of Clinical Pharmacology, 47(10), 1311-1319, Oct. 2007.

Olney et al., AVP-923, A Combination of Dextromethorphan Hydrobromide and Quinidine Sulfate for the Treatment of Pseudobulbar Affect and Neuropathic Pain, IDrugs: The Investigational Drugs Journal, 13(4), 254-265, Apr. 2010.

Rosen, Dextromethorphan/Quinidine Sulfate (Zenvia™) for Pseudobulbar Affect, Drugs of Today, 44(9), 661-668, Sep. 2008.

Rowley, Regulatory History and Background on Over-the-Counter Dextromethorphan, FDA Drug Safety and Risk Management Advisory Committee Meeting, Presentation, 21 pgs., Sep. 14, 2010.

Semenchuk et al., Efficacy of Sustained-Release Bupropion in Neuropathic Pain: An Open-Label Study, The Clinical Journal of Pain, 16(1), Mar. 6-11, 2000.

Struthers et al., Mecamylamine, Dihydro-β-Erythroidine, and Dextromethorphan Block Conditioned Responding Evoked by the Conditional Stimulus Effects of Nicotine, Pharmacology, Biochemistry and Behavior, 94(2), 319-328, Dec. 2009.

U.S. Appl. No. 13/478,023, filed May 22, 2012 First Named Inventor Heniot Tabuteau Assignee: Antecip Bioventures II LLC.

U.S. Appl. No. 14/863,284, filed Sep. 23, 2015 First Named Inventor Herriot Tabuteau Assignee: Antecip Bioventures II LLC.

U.S. Appl. No. 14/878,998, filed Oct. 8, 2015 First Named Inventor Herriot Tabuteau Assignee: Antecip Bioventures II LLC.

U.S. Appl. No. 14/978,976, filed Dec. 22, 2015 First Named Inventor Herriot Tabuteau Assignee: Antecip Bioventures II LLC.

U.S. Appl. No. 14/997,316, filed Jan. 15, 2016 First Named Inventor Herriot Tabuteau Assignee: Antecip Bioventures II LLC.

U.S. Appl. No. 15/057,983, filed Mar. 1, 2016 First Named Inventor Herriot Tabuteau Assignee: Antecip Bioventures II LLC.

Wadhwa et al., Large-Dose Oral Dextromethorphan as an Adjunct to Patient-Controlled Analgesia with Morphine after Knee Surgery, Anesthesia & Analgesia, 92(2), 448-454, Feb. 2001.

Walker et al., An Open Label Trial of Dextromethorphan in Huntington's Disease, Clinical Neuropharmacology, 12 (4), 322-330, Aug. 1989.

\* cited by examiner

COMPOSITIONS AND METHODS COMPRISING ERYTHROHYDROXYBUPROPION AND RELATED COMPOUNDS FOR IMPROVING THE EFFICACY OF DEXTROMETHORPHAN

SUMMARY

Some embodiments include method of decreasing the number of doses of dextromethorphan that can be administered while increasing efficacy, comprising orally administering an effective amount of erythrohydroxybupropion or a prodrug thereof to a human being in need of treatment with dextromethorphan.

Some embodiments include a method of reducing an adverse event associated with treatment by dextromethorphan, comprising co-administering erythrohydroxybupropion, or a prodrug thereof, and dextromethorphan to a human patient in need of dextromethorphan treatment, wherein the human patient is at risk of experiencing the adverse event as a result being treated with dextromethorphan.

Some embodiments include a method of decreasing dextrorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of treatment with dextromethorphan, wherein a decrease in the dextrorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of decreasing dextrorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of treatment with dextromethorphan, wherein a decrease in the dextrorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of decreasing dextrorphan plasma levels comprising co-administering bupropion and dextromethorphan to a human being in need of treatment with dextromethorphan, wherein the bupropion is administered on the first day of at least two days of treatment with dextromethorphan, wherein a decrease in the dextrorphan plasma level occurs on the first day that bupropion and dextromethorphan are co-administered, as compared to the same amount of dextromethorphan administered without bupropion.

Some embodiments include a method of decreasing dextrorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of treatment with dextromethorphan, wherein a decrease in the dextrorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of decreasing dextrorphan plasma levels comprising co-administering bupropion and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion for eight consecutive days.

Some embodiments include a method of decreasing dextrorphan plasma levels comprising co-administering hydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without hydroxybupropion, or a prodrug thereof, for eight consecutive days.

Some embodiments include a method of decreasing dextrorphan plasma levels comprising co-administering erythrohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without erythrohydroxybupropion, or a prodrug thereof, for eight consecutive days.

Some embodiments include a method of decreasing dextrorphan plasma levels comprising co-administering threohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without threohydroxybupropion, or a prodrug thereof, for eight consecutive days.

Antidepressant compounds, such as bupropion, hydroxybupropion, erythrohydroxybupropion, threohydroxybupropion, or a metabolite or prodrug of any of these compounds, can be used to improve the therapeutic properties, such as in the treatment of neurological disorders, of dextromethorphan. Bupropion, hydroxybupropion, erythrohydroxybupropion, threohydroxybupropion, or a metabolite or prodrug of any of these compounds, regardless of stereochemistry, can be effective in inhibiting or reducing the metabolism of dextromethorphan in some human beings. This may be accomplished by co-administering bupropion, hydroxybupropion, erythrohydroxybupropion, threohydroxybupropion, or a metabolite or prodrug of any of these compounds, and dextromethorphan.

Some embodiments include a method of treating a neurological disorder comprising administering an antidepressant compound and dextromethorphan to a human being in need thereof, wherein the human being is an extensive metabolizer of dextromethorphan.

Some embodiments include a method of increasing dextromethorphan plasma levels in a human being in need of treatment with dextromethorphan, wherein the human being is an extensive metabolizer of dextromethorphan, comprising co-administering bupropion with dextromethorphan to the human being.

Some embodiments include a method of inhibiting the metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of increasing the metabolic lifetime of dextromethorphan, comprising administering bupropion to a human being in need of treatment with dextromethorphan, wherein the human being is an extensive metabolizer of dextromethorphan, and wherein dextromethorphan is present in the body of the human being at the same time as bupropion.

Some embodiments include a method of correcting extensive metabolism of dextromethorphan, comprising administering bupropion to a human being in need thereof.

Some embodiments include a method of improving the antitussive properties of dextromethorphan comprising administering bupropion in conjunction with administration of dextromethorphan to a human being in need of treatment for cough.

Some embodiments include a method of treating cough comprising administering a combination of bupropion and dextromethorphan to a human being in need thereof.

Some embodiments include a method of treating a neurological disorder comprising administering bupropion and dextromethorphan to a human being in need thereof, wherein the bupropion and dextromethorphan are administered at least once a day for at least 8 days.

Some embodiments include a method of treating a neurological disorder comprising administering about 150 mg/day to about 300 mg/day of bupropion and about 15 mg/day to about 60 mg/day of dextromethorphan to a human being in need thereof.

Some embodiments include a method of increasing dextromethorphan plasma levels in a human being in need of treatment with dextromethorphan, wherein the human being is an extensive metabolizer of dextromethorphan, comprising co-administering hydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering erythrohydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering threohydroxybupropion, or a prodrug thereof, with dextromethorphan to the human being.

Some embodiments include a method of inhibiting metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of inhibiting metabolism of dextromethorphan, comprising administering hydroxybupropion, or a prodrug thereof, to a human being, wherein the human being is an extensive metabolizer of dextromethorphan, and wherein dextromethorphan is present in the body of the human being at the same time as hydroxybupropion.

Some embodiments include a method of inhibiting metabolism of dextromethorphan, comprising administering erythrohydroxybupropion, or a prodrug thereof, to a human being, wherein the human being is an extensive metabolizer of dextromethorphan, and wherein dextromethorphan is present in the body of the human being at the same time as erythrohydroxybupropion.

Some embodiments include a method of inhibiting metabolism of dextromethorphan, comprising administering threohydroxybupropion, or a prodrug thereof, to a human being, wherein the human being is an extensive metabolizer of dextromethorphan, and wherein dextromethorphan is present in the body of the human being at the same time as threohydroxybupropion.

Some embodiments include a method of increasing the metabolic lifetime of dextromethorphan, comprising administering hydroxybupropion, or a prodrug thereof, to a human being in need of treatment with dextromethorphan, wherein the human being is an extensive metabolizer of dextromethorphan, and wherein dextromethorphan is present in the body of the human being at the same time as hydroxybupropion.

Some embodiments include a method of increasing the metabolic lifetime of dextromethorphan, comprising administering erythrohydroxybupropion, or a prodrug thereof, to a human being in need of treatment with dextromethorphan, wherein the human being is an extensive metabolizer of dextromethorphan, and wherein dextromethorphan is present in the body of the human being at the same time as erythrohydroxybupropion.

Some embodiments include a method of increasing the metabolic lifetime of dextromethorphan, comprising administering threohydroxybupropion, or a prodrug thereof, to a human being in need of treatment with dextromethorphan, wherein the human being is an extensive metabolizer of dextromethorphan, and wherein dextromethorphan is present in the body of the human being at the same time as threohydroxybupropion.

Some embodiments include a method of increasing dextromethorphan plasma levels comprising co-administering bupropion and dextromethorphan to a human being in need of treatment with dextromethorphan, wherein the bupropion is administered on the first day of at least two days of co-administration of bupropion with dextromethorphan, wherein an increase in the dextromethorphan plasma level occurs on the first day that bupropion and dextromethorphan are co-administered, as compared to the same amount of dextromethorphan administered without bupropion.

Some embodiments include a method of increasing dextromethorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of co-administration of hydroxybupropion, or a prodrug thereof, with dextromethorphan, wherein an increase in the dextromethorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of increasing dextromethorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of co-administration of erythrohydroxybupropion, or a prodrug thereof, with dextromethorphan, wherein an increase in the dextromethorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of increasing dextromethorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of co-administration of threohydroxybupropion, or a prodrug thereof, with dextromethorphan, wherein an increase in the dextromethorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of increasing dextromethorphan plasma levels comprising co-administering bupropion and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion for five consecutive days.

Some embodiments include a method of increasing dextromethorphan plasma levels comprising co-administering hydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without hydroxybupropion, or a prodrug thereof, for five consecutive days.

Some embodiments include a method of increasing dextromethorphan plasma levels comprising co-administering erythrohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without erythrohydroxybupropion, or a prodrug thereof, for five consecutive days.

Some embodiments include a method of increasing dextromethorphan plasma levels comprising co-administering threohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without threohydroxybupropion, or a prodrug thereof, for five consecutive days.

Some embodiments include a method of increasing dextromethorphan plasma levels comprising co-administering bupropion and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion for six consecutive days.

Some embodiments include a method of increasing dextromethorphan plasma levels comprising co-administering hydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without hydroxybupropion, or a prodrug thereof, for six consecutive days.

Some embodiments include a method of increasing dextromethorphan plasma levels comprising co-administering erythrohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without erythrohydroxybupropion, or a prodrug thereof, for six consecutive days.

Some embodiments include a method of increasing dextromethorphan plasma levels comprising co-administering threohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without threohydroxybupropion, or a prodrug thereof, for six consecutive days.

Some embodiments include a method of reducing a trough effect of dextromethorphan comprising, co-administering bupropion with dextromethorphan to a human patient in need of treatment with dextromethorphan, wherein dextromethorphan has a plasma level 12 hours after co-administering bupropion with dextromethorphan that is at least twice the plasma level that would be achieved by administering the same amount of dextromethorphan without bupropion.

Some embodiments include a method of reducing a trough effect of dextromethorphan comprising, co-administering hydroxybupropion, or a prodrug thereof, with dextromethorphan to a human patient in need of treatment with dextromethorphan, wherein dextromethorphan has a plasma level 12 hours after co-administering hydroxybupropion, or a prodrug thereof, with dextromethorphan that is at least twice the plasma level that would be achieved by administering the same amount of dextromethorphan without hydroxybupropion or a prodrug thereof.

Some embodiments include a method of reducing a trough effect of dextromethorphan comprising, co-administering erythrohydroxybupropion, or a prodrug thereof, with dextromethorphan to a human patient in need of treatment with dextromethorphan, wherein dextromethorphan has a plasma level 12 hours after co-administering erythrohydroxybupropion, or a prodrug thereof, with dextromethorphan that is at least twice the plasma level that would be achieved by administering the same amount of dextromethorphan without erythrohydroxybupropion or a prodrug thereof.

Some embodiments include a method of reducing a trough effect of dextromethorphan comprising, co-administering threohydroxybupropion, or a prodrug thereof, with dextromethorphan to a human patient in need of treatment with dextromethorphan, wherein dextromethorphan has a plasma level 12 hours after co-administering threohydroxybupropion, or a prodrug thereof, with dextromethorphan that is at least twice the plasma level that would be achieved by administering the same amount of dextromethorphan without threohydroxybupropion or a prodrug thereof.

Some embodiments include a method of reducing an adverse event associated with treatment by dextromethorphan, comprising co-administering bupropion and dextrometorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering hydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering erythrohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering threohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by bupropion, comprising co-administering dextromethorphan and bupropion to a human patient in need of bupropion treatment, wherein the human patient is at risk of experiencing the adverse event as a result of being treated with bupropion.

Some embodiments include a method of correcting extensive metabolism of dextromethorphan, comprising administering hydroxybupropion, or a prodrug thereof, to a human being in need thereof.

Some embodiments include a method of correcting extensive metabolism of dextromethorphan, comprising administering erythrohydroxybupropion, or a prodrug thereof, to a human being in need thereof.

Some embodiments include a method of correcting extensive metabolism of dextromethorphan, comprising administering threohydroxybupropion, or a prodrug thereof, to a human being in need thereof.

Some embodiments include a method of improving antitussive properties of dextromethorphan comprising administering bupropion in conjunction with administration of dextromethorphan to a human being in need of treatment for cough.

Some embodiments include a method of improving antitussive properties of dextromethorphan comprising administering hydroxybupropion, or a prodrug thereof, in conjunction with administration of dextromethorphan to a human being in need of treatment for cough.

Some embodiments include a method of improving antitussive properties of dextromethorphan comprising administering erythrohydroxybupropion, or a prodrug thereof, in conjunction with administration of dextromethorphan to a human being in need of treatment for cough.

Some embodiments include a method of improving antitussive properties of dextromethorphan comprising administering threohydroxybupropion, or a prodrug thereof, in conjunction with administration of dextromethorphan to a human being in need of treatment for cough.

Some embodiments include a method of treating cough comprising administering a combination of hydroxybupropion, or a prodrug thereof, and dextromethorphan to a human being in need thereof.

Some embodiments include a method of treating cough comprising administering a combination of erythrohydroxybupropion, or a prodrug thereof, and dextromethorphan to a human being in need thereof.

Some embodiments include a method of treating cough comprising administering a combination of threohydroxybupropion, or a prodrug thereof, and dextromethorphan to a human being in need thereof.

Some embodiments include a method of treating a neurological disorder comprising administering bupropion and dextromethorphan to a human being in need thereof, wherein the bupropion and dextromethorphan are administered at least once a day for at least 8 days.

Some embodiments include a method of treating a neurological disorder comprising administering hydroxybupropion, or a prodrug thereof, and dextromethorphan to a human being in need thereof, wherein the bupropion and dextromethorphan are administered at least once a day for at least 8 days.

Some embodiments include a method of treating a neurological disorder comprising administering erythrohydroxybupropion, or a prodrug thereof, and dextromethorphan to a human being in need thereof, wherein the bupropion and dextromethorphan are administered at least once a day for at least 8 days.

Some embodiments include a method of treating a neurological disorder comprising administering threohydroxybupropion, or a prodrug thereof, and dextromethorphan to a human being in need thereof, wherein the bupropion and dextromethorphan are administered at least once a day for at least 8 days.

Some embodiments include an oral sustained release delivery system for dextromethorphan, comprising bupropion, hydroxybupropion, erythrohydroxybupropion, threohydroxybupropion, or a prodrug of any of these compounds, dextromethorphan, and a water soluble vehicle.

Some embodiments include a method of decreasing the number of doses of dextromethorphan that can be administered without loss of efficacy, comprising orally administering an effective amount of bupropion, hydroxybupropion, erythrohydroxybupropion, threohydroxybupropion, or a prodrug of any of these compounds, to a human being in need of treatment with dextromethorphan.

Some embodiments include a pharmaceutical composition, dosage form, or medicament comprising a therapeutically effective amount of dextromethorphan, a therapeutically effective amount of an antidepressant, such as bupropion, hydroxybupropion, erythrohydroxybupropion, threohydroxybupropion, or a metabolite or prodrug of any of these compounds, and a pharmaceutically acceptable excipient.

DETAILED DESCRIPTION

Figure 1:
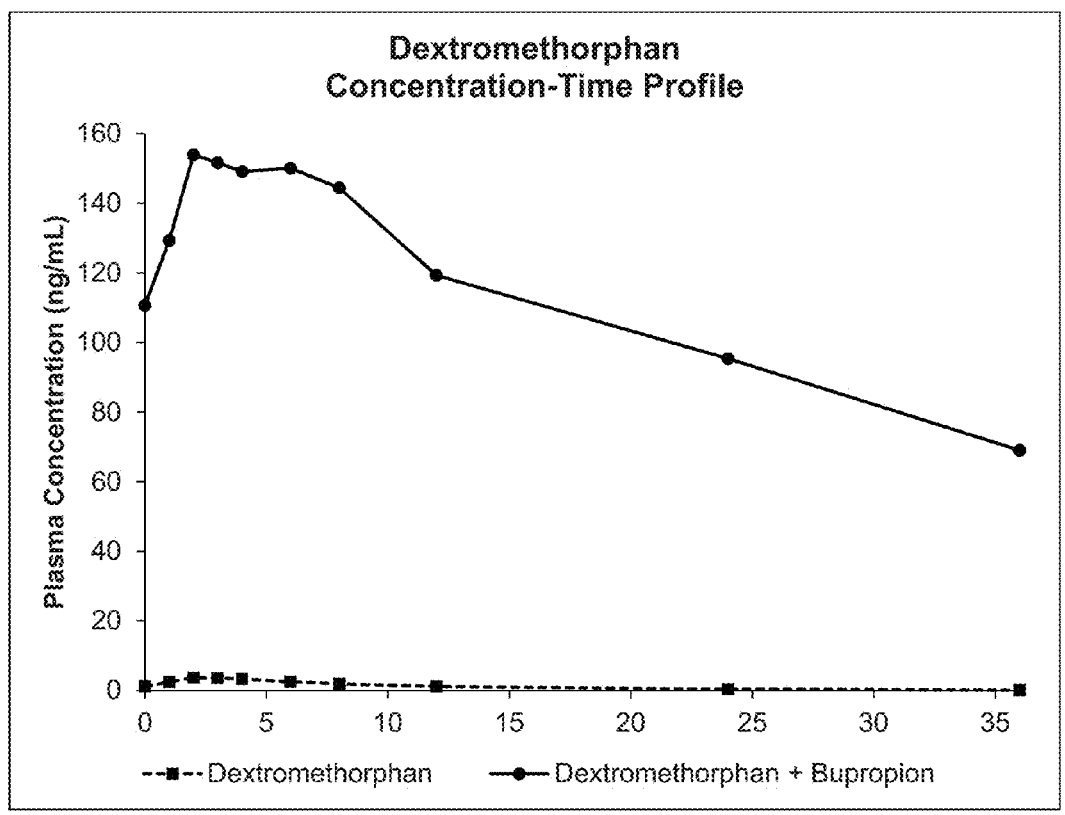
FIG. 1 is a plot of the mean plasma concentrations of dextromethorphan over time after dosing on Day 8 for subjects administered dextromethorphan alone or dextromethorphan and bupropion.

Some embodiments include a method of treating neurological disorders comprising administering a therapeutically effective amount of dextromethorphan and a therapeutically effective amount of an antidepressant, such as bupropion, hydroxybupropion, erythrohydroxybupropion, threohydroxybupropion, or a metabolite or prodrug of any of these compounds, to a person in need thereof.

Some embodiments include a method of enhancing the therapeutic properties of dextromethorphan in treating neurological disorders, comprising co-administering dextromethorphan and an antidepressant, such as bupropion, hydroxybupropion, erythrohydroxybupropion, threohydroxybupropion, or a metabolite or prodrug of any of these compounds.

Some embodiments include a method of increasing dextromethorphan plasma levels in a human being that is an extensive metabolizer of dextromethorphan, comprising co-administering an antidepressant compound, such as bupropion, and dextromethorphan to the human being.

Some embodiments include a method of inhibiting the metabolism of dextromethorphan, comprising administering an antidepressant compound, such as bupropion, to a human being, wherein the human being is an extensive metabolizer of dextromethorphan, and wherein dextromethorphan is present in the body of the human being at the same time as the antidepressant.

Some embodiments include a method of increasing the metabolic lifetime of dextromethorphan, including increasing the elimination half life ($T_{1/2}$) of dextromethorphan. These embodiments may comprise administering an antidepressant compound, such as bupropion, to a human being, wherein the human being is an extensive metabolizer of dextromethorphan, and wherein dextromethorphan is present in the body of the human being at the same time as the antidepressant compound.

Some embodiments include a method of correcting extensive metabolism of dextromethorphan, comprising administering an antidepressant compound, such as bupropion, to a human being in need thereof, such as a human being in need of treatment for pain.

Some embodiments include a method of improving the therapeutic properties of dextromethorphan in treating neurological disorders comprising administering an antidepressant compound, such as bupropion, in conjunction with administration of dextromethorphan to a human being in need of treatment for a neurological disorder.

Some embodiments include a method of treating neurological disorders comprising administering a combination of an antidepressant compound, such as bupropion, and dextromethorphan to a human being in need thereof.

Dextromethorphan has the structure shown below.

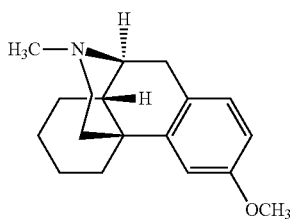

Dextromethorphan is used as a cough suppressant. According to the FDA's dextromethorphan product labeling requirement under the OTC Monograph [21CFR341.74], dextromethorphan should be dosed 6 times a day (every 4 hours), 4 times a day (every 6 hours), or 3 times a day (every 8 hours).

Dextromethorphan is rapidly metabolized in the human liver. This rapid hepatic metabolism may limit systemic drug exposure in individuals who are extensive metabolizers. Human beings can be: 1) extensive metabolizers of dextromethorphan—those who rapidly metabolize dextromethorphan; 2) poor metabolizers of dextromethorphan—those who only poorly metabolize dextromethorphan; or 3) intermediate metabolizers of dextromethorphan—those whose metabolism of dextromethorphan is somewhere between that of an extensive metabolizer and a poor metabolizer. Extensive metabolizers can also be ultra-rapid metabolizers. Extensive metabolizers of dextromethorphan are a significant portion of the human population. Dextromethorphan can, for example, be metabolized to dextrorphan.

When given the same oral dose of dextromethorphan, plasma levels of dextromethorphan are significantly higher in poor metabolizers or intermediate metabolizers as compared to extensive metabolizers of dextromethorphan. The low plasma concentrations of dextromethorphan can limit its clinical utility as a single agent for extensive metabolizers, and possibly intermediate metabolizers, of dextromethorphan. Some antidepressants, such as bupropion, inhibit the metabolism of dextromethorphan, and can thus improve its therapeutic efficacy. Similarly, antidepressants may allow dextromethorphan to be given less often, such as once a day instead of twice a day, once a day instead of three times a day, once a day instead of four times a day, twice a day instead of three times a day, or twice a day instead of four times a day, without loss of therapeutic efficacy.

Pain or other neurological disorders may be treated by a method comprising administering a therapeutically effective amount of dextromethorphan and a therapeutically effective amount of an antidepressant compound, such as bupropion, hydroxybupropion, erythrohydroxybupropion, threohydroxybupropion, or a metabolite or prodrug of any of these compounds, to a person in need thereof.

Examples of neurological disorders that may be treated, or that may be treated with increased efficacy, by a combination of dextromethorphan and an antidepressant such as bupropion, hydroxybupropion, erythrohydroxybupropion, threohydroxybupropion, or a metabolite or prodrug of any of these compounds, include, but are not limited to: affective disorders, psychiatric disorders, cerebral function disorders, movement disorders, dementias, motor neuron diseases, neurodegenerative diseases, seizure disorders, and headaches.

Affective disorders that may be treated by a combination of dextromethorphan and an antidepressant such as bupropion, hydroxybupropion, erythrohydroxybupropion, threohydroxybupropion, or a metabolite or prodrug of any of these compounds, include, but are not limited to, depression, major depression, treatment-resistant depression and treatment-resistant bipolar depression, bipolar disorders including cyclothymia, seasonal affective disorder, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by changes in mood, feelings of intense sadness, despair, mental slowing, loss of concentration, pessimistic worry, agitation, and self-deprecation. Physical symptoms of depression may include insomnia, anorexia, weight loss, decreased energy and libido, and abnormal hormonal circadian rhythms.

Psychiatric disorders that may be treated by a combination of dextromethorphan and an antidepressant such as bupropion, hydroxybupropion, erythrohydroxybupropion, threohydroxybupropion, or a metabolite or prodrug of any of these compounds, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Substance addiction abuse that may be treated by a combination of dextromethorphan and an antidepressant such as bupropion, hydroxybupropion, erythrohydroxybupropion, threohydroxybupropion, or a metabolite or prodrug of any of these compounds, includes, but is not limited to, drug dependence, addiction to cocaine, psychostimulants (e.g., crack, cocaine, speed, meth), nicotine, alcohol, opioids, anxiolytic and hypnotic drugs, *cannabis* (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that may be treated by a combination of dextromethorphan and an antidepressant such as bupropion, hydroxybupropion, erythrohydroxybupropion, threohydroxybupropion, or a metabolite or prodrug of any of these compounds include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that may be treated by a combination of dextromethorphan and an antidepressant such as bupropion, hydroxybupropion, erythrohydroxybupropion, threohydroxybupropion, or a metabolite or prodrug of any of these compounds include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by a combination of dextromethorphan and an antidepressant such as bupropion, hydroxybupropion, erythrohydroxybupropion, threohydroxybupropion, or a metabolite or prodrug of any of these compounds include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by a combination of dextromethorphan and an antidepressant such as bupropion, hydroxybupropion, erythrohydroxybupropion, threohydroxybupropion, or a metabolite or prodrug of any of these compounds include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated by a combination of dextromethorphan and an antidepressant such as bupropion, hydroxybupropion, erythrohydroxybupropion, threohydroxybupropion, or a metabolite or prodrug of any of these compounds include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by a combination of dextromethorphan and an antidepressant such as bupropion, hydroxybupropion, erythrohydroxybupropion, threohydroxybupropion, or a metabolite or prodrug of any of these compounds include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by a combination of dextromethorphan and an antidepressant such as bupropion, hydroxybupropion, erythrohydroxybupropion, threohydroxybupropion, or a metabolite or prodrug of any of these compounds include, but are not limited to, migraine, tension, and cluster headaches.

Other neurological disorders that may be treated by a combination of dextromethorphan and an antidepressant such as bupropion, hydroxybupropion, erythrohydroxybupropion, threohydroxybupropion, or a metabolite or prodrug of any of these compounds include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, a combination of dextromethorphan and an antidepressant such as bupropion, hydroxybupropion, erythrohydroxybupropion, threohydroxybupropion, or a metabolite or prodrug of any of these compounds, may be used to treat pain, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, a combination of dextromethorphan and an antidepressant such as bupropion, hydroxybupropion, erythrohydroxybupropion, threohydroxybupropion, or a metabolite or prodrug of any of these compounds may be used to treat dermatitis.

Pain relieving properties of dextromethorphan may be enhanced by a method comprising co-administering dextromethorphan and an antidepressant, such as bupropion, hydroxybupropion, erythrohydroxybupropion, threohydroxybupropion, or a metabolite or prodrug of any of these compounds, with dextromethorphan.

Pain relieving properties of bupropion may be enhanced by a method comprising co-administering dextromethorphan with bupropion, hydroxybupropion, erythrohydroxybupropion, threohydroxybupropion, or a metabolite or prodrug of any of these compounds.

These methods may be used to treat, or provide relief to, any type of pain including, but not limited to, musculoskeletal pain, neuropathic pain, cancer-related pain, acute pain, nociceptive pain, etc.

Examples of musculoskeletal pain include low back pain (i.e. lumbosacral pain), primary dysmenorrhea, and arthritic pain, such as pain associated with rheumatoid arthritis, juvenile rheumatoid arthritis, osteoarthritis, axial spondyloarthritis including ankylosing spondylitis, etc.

In some embodiments, a combination of dextromethorphan and an antidepressant, such as bupropion, is used to treat chronic musculoskeletal pain.

Examples of neuropathic pain include diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemo-therapy associated neuropathy, etc.

The term "treating" or "treatment" includes the diagnosis, cure, mitigation, treatment, or prevention of disease in man or other animals, or any activity that otherwise affects the structure or any function of the body of man or other animals.

Any antidepressant may be used in combination with dextromethorphan to improve the therapeutic properties of dextromethorphan. Dextromethorphan and the antidepressant compound may be administered in separate compositions or dosage forms, or may be administered in a single composition or dosage form comprising both.

Antidepressant compounds that can be co-administered with dextromethorphan include, but are not limited to, bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, etc., or a metabolite or prodrug of any of these compounds, or a pharmaceutically acceptable salt of any of these compounds.

Bupropion has the structure shown below (bupropion hydrochloride form shown).

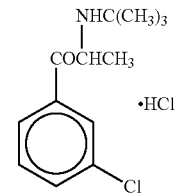

Combining bupropion with dextromethorphan may provide greater efficacy, such as greater pain relief, than would otherwise be achieved by administering either component alone. In extensive metabolizers, dextromethorphan can be rapidly and extensively metabolized, yielding low systemic exposure even at high doses. Bupropion, besides possessing antidepressant and analgesic properties, is an inhibitor of dextromethorphan metabolism. Metabolites of bupropion, which include hydroxybupropion, threohydroxybupropion (also known as threohydrobupropion or threodihydrobupropion), and erythrohydroxybupropion (also known as erythrohydrobupropion or erythrodihydrobupropion), are also inhibitors of dextromethorphan metabolism. Thus, bupropion, including a form of bupropion that is rapidly converted in the body (such as a salt, hydrate, solvate, polymorph, etc.), is a prodrug of hydroxybupropion, threohydroxybupropion, and erythrohydroxybupropion.

As explained above, this inhibition may augment dextromethorphan plasma levels, resulting in additive or synergistic efficacy such as relief of neurological disorders including pain, depression, smoking cessation, etc. Thus, while inhibition of dextromethorphan metabolism is only one of many potential benefits of the combination, co-administration of dextromethorphan with bupropion may thereby enhance the efficacy of bupropion for many individuals. Co-administration of dextromethorphan with bupropion may enhance the analgesic properties of bupropion for many individuals. Co-administration of dextromethorphan with bupropion may also enhance the antidepressant properties of bupropion for many individuals, including faster onset of action.

Another potential benefit of co-administration of dextromethorphan and bupropion is that it may be useful to reduce the potential for an adverse event, such as somnolence, associated with treatment by dextromethorphan. This may be useful, for example, in human patients at risk of experiencing the adverse event as a result being treated with dextromethorphan.

Another potential benefit of co-administration of dextromethorphan and bupropion is that it may be useful to reduce the potential for an adverse event, such as seizure, associated with treatment by bupropion, hydroxybupropion, erythrohydroxybupropion, threohydroxybupropion, or a metabolite or prodrug of any of these compounds. This may be useful, for example, in human patients at risk of experiencing the adverse event as a result being treated with bupropion, hydroxybupropion, erythrohydroxybupropion, threohydroxybupropion, or a metabolite or prodrug of any of these compounds.

With respect to dextromethorphan, bupropion, hydroxybupropion, erythrohydroxybupropion, threohydroxybupropion, or a metabolite or prodrug of any of these compounds, co-administration may reduce a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and tongue protrusion.

Gastrointestinal adverse events include, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

Co-administering dextromethorphan and an antidepressant, such as bupropion, hydroxybupropion, erythrohydroxybupropion, threohydroxybupropion, or a metabolite or prodrug of any of these compounds, does not necessarily require that the two compounds be administered in the same dosage form. For example, the two compounds may be administered in a single dosage form, or they may be administered in two separate dosage forms. Additionally, the two compounds may be administered at the same time, but this is not required. The compounds can be given at different times as long as both are in a human body at the same time for at least a portion of the time that treatment by co-administration is being carried out.

In some embodiments, co-administration of a combination of bupropion, hydroxybupropion, erythrohydroxybupropion, threohydroxybupropion, or a metabolite or prodrug of any of these compounds, and dextromethorphan results in both bupropion, hydroxybupropion, erythrohydroxybupropion, threohydroxybupropion, or a metabolite or prodrug of any of these compounds, and dextromethorphan contributing to the pain relieving properties of the combination. For example, the combination may have improved pain relieving properties as compared to bupropion, hydroxybupropion, erythrohydroxybupropion, threohydroxybupropion, or a metabolite or prodrug of any of these compounds, alone or compared to dextromethorphan alone, including potentially faster onset of action.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to bupropion, hydroxybupropion, erythrohydroxybupropion, threohydroxybupropion, or a metabolite or prodrug of any of these compounds, alone.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to as compared to dextromethorphan alone.

Unless otherwise indicated, any reference to a compound herein, such as dextromethorphan, bupropion, hydroxybupropion, erythrohydroxybupropion, threohydroxybupropion, by structure, name, or any other means, includes pharmaceutically acceptable salts; alternate solid forms, such as polymorphs, solvates, hydrates, etc.; tautomers; deuterium modified compounds, such as deuterium modified dextromethorphan; or any chemical species that may rapidly convert to a compound described herein under conditions in which the compounds are used as described herein.

Examples of deuterium modified dextromethorphan include, but are not limited to, those shown below.

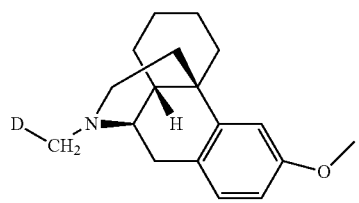

-continued

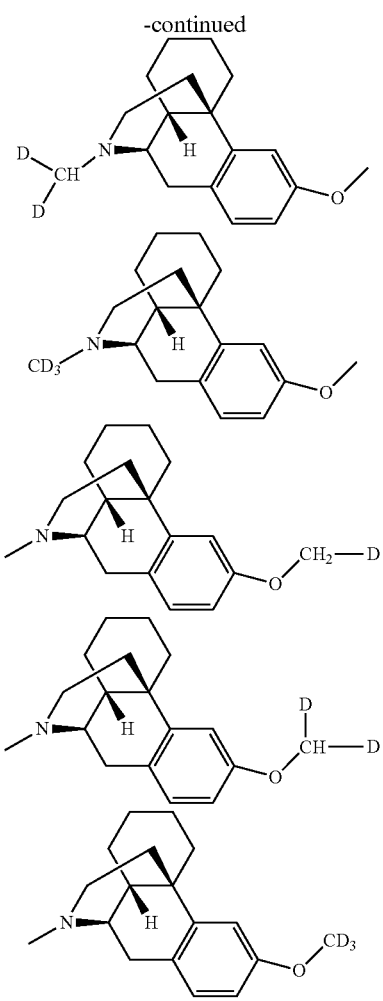

A dosage form or a composition may be a blend or mixture of dextromethorphan and a compound that inhibits the metabolism of dextromethorphan, such as bupropion, hydroxybupropion, erythrohydroxybupropion, threohydroxybupropion, or a metabolite or prodrug of any of these compounds, either alone or within a vehicle. For example, dextromethorphan and bupropion may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, dextromethorphan and bupropion may be substantially uniformly dispersed within a composition or dosage form. Alternatively, dextromethorphan and bupropion may be in separate domains or phases within a composition or dosage form. For example, one drug may be in a coating and another drug may be in a core within the coating. For example, one drug may be formulated for sustained release and another drug may be formulated for immediate release.

Some embodiments include administration of a tablet that contains bupropion in a form that provides sustained release and dextromethorphan in a form that provides immediate release. While there are many ways that sustained release of bupropion may be achieved, in some embodiments bupropion is combined with hydroxypropyl methylcellulose. For example, particles of bupropion hydrochloride could be blended with microcrystalline cellulose and hydroxypropyl methylcellulose (e.g METHOCEL®) to form an admixture of blended powders. This could then be combined with immediate release dextromethorphan in a single tablet.

Dextromethorphan and/or an antidepressant, such as bupropion, hydroxybupropion, threohydroxybupropion and erythrohydroxybupropion, or a non-bupropion antidepressant (all of which are referred to collectively herein as "therapeutic compounds" for convenience) may be combined with a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a human patient in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The ratio of dextromethorphan to bupropion may vary. In some embodiments, the weight ratio of dextromethorphan to bupropion may be about 0.1 to about 10, about 0.1 to about 2, about 0.2 to about 1, about 0.1 to about 0.5, about 0.1 to about 0.3, about 0.2 to about 0.4, about 0.3 to about 0.5, about 0.5 to about 0.7, about 0.8 to about 1, about 0.2 to about 0.3, about 0.4, about 0.45, about 0.6, about 0.9, or any ratio in a range bounded by, or between, any of these values. A ratio of 0.1 indicates that the weight of dextromethorphan is 1/10 that of bupropion. A ratio of 10 indicates that the weight of dextromethorphan is 10 times that of bupropion.

The amount of dextromethorphan in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of dextromethorphan.

Some liquid dosage forms may contain about 10 mg to about 500 mg, about 30 mg to about 350 mg, about 50 mg to about 200 mg, about 50 mg to about 70 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 80 mg to about 100 mg, about 110 mg to about 130 mg, about 170 mg to about 190 mg, about 45 mg, about 60 mg, about 90 mg, about 120 mg, or about 180 mg of dextromethorphan, or any amount of dextromethorphan in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of dextromethorphan.

Some solid dosage forms may contain about 10 mg to about 500 mg, about 30 mg to about 350 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 50 mg to about 200 mg, about 50 mg to about 70 mg, about 80 mg to about 100 mg, about 110 mg to about 130 mg, about 170 mg to about 190 mg, about 60 mg, about 90 mg, about 120 mg, or about 180 mg of dextromethorphan, or any amount of dextromethorphan in a range bounded by, or between, any of these values.

The amount of bupropion, hydroxybupropion, erythrohydroxybupropion, threohydroxybupropion, or a metabolite or prodrug of any of these compounds, in a therapeutic composition may vary. If increasing the plasma level of dextromethorphan is desired, bupropion, hydroxybupropion, erythrohydroxybupropion, threohydroxybupropion, or a metabolite or prodrug of any of these compounds, should be administered in an amount that increases the plasma level of dextromethorphan. For example, bupropion, hydroxybupropion, erythrohydroxybupropion, threohydroxybupropion, or a metabolite or prodrug of any of these compounds, may be administered in an amount that results in a plasma concentration of dextromethorphan in the human being, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times, the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may administered to a human being in an amount that results in a 12 hour area under the curve from the time of dosing ($AUC_{0-12}$), or average plasma concentration in the human being for the 12 hours following dosing ($C_{avg}$) of dextromethorphan, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may administered to a human being in an amount that results in a maximum plasma concentration ($C_{max}$) of dextromethorphan in the human being, on day 8, that is at least about 2 times, at least about 5 times, at least about 10 times, at least about 15 times, at least about 20 times, at least about 30 times, or at least about 40 times the plasma concentration of the same amount of dextromethorphan administered without bupropion, hydroxybupropion, erythrohydroxybupropion, threohydroxybupropion, or a metabolite or prodrug of any of these compounds.

For co-administration of bupropion, hydroxybupropion, threohydroxybupropion, erythrohydroxybupropion, or a metabolite or prodrug of any of these compounds, an increase in the dextromethorphan plasma level can occur on the first day that bupropion, hydroxybupropion, threohydroxybupropion, erythrohydroxybupropion, or a metabolite or prodrug of any of these compounds, is administered, as compared to the same amount of dextromethorphan administered without bupropion, hydroxybupropion, threohydroxybupropion, erythrohydroxybupropion, or a metabolite of prodrug of any of these compounds. For example, the dextromethorphan plasma level on the first day that bupropion, hydroxybupropion, threohydroxybupropion, erythrohydroxybupropion, or a metabolite or prodrug of any of these compounds, is administered may be at least about 1.5 times, at least about at least 2 times, at least about 2.5 times, at least about 3 times, at least about 4 times, at least about 5 times, at least about 6 times at least about 7 times, at least about 8 times, at least about 9 times, or at least about 10 times the level that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan AUC on the first day that bupropion, hydroxybupropion, threohydroxybupropion, erythrohydroxybupropion, or a metabolite or prodrug of any of these compounds, is administered may be at least twice the AUC that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $C_{max}$ on the first day that bupropion, hydroxybupropion, threohydroxybupropion, erythrohydroxybupropion, or a metabolite or prodrug of any of these compounds, is administered may be at least twice the $C_{max}$ that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan trough level (e.g., plasma level 12 hours after administration) on the first day that bupropion, hydroxybupropion, threohydroxybupropion, erythrohydroxybupropion, or a metabolite or prodrug of any of these compounds, is administered may be at least twice the trough level that would be achieved by administering the same amount of dextromethorphan without bupropion, hydroxybupropion, threohydroxybupropion, erythrohydroxybupropion, or a metabolite or prodrug of any of these compounds.

In some embodiments, bupropion, hydroxybupropion, threohydroxybupropion, erythrohydroxybupropion, or a metabolite or prodrug of any of these compounds, is administered on the first day of at least two days of treatment with dextromethorphan, wherein a decrease in the dextrorphan plasma level occurs on the first day that bupropion, hydroxybupropion, threohydroxybupropion, erythrohydroxybupropion, or a metabolite or prodrug of any of these compounds, and dextromethorphan are co-administered, as compared to the same amount of dextromethorphan administered without bupropion, hydroxybupropion, threohydroxybupropion, erythrohydroxybupropion, or a metabolite or prodrug of any of these compounds. For example, the dextrorphan plasma level on the first day may be reduced by at least 5% as compared to the dextrorphan plasma level that would be achieved by administering the same amount of dextromethorphan without bupropion.

In some embodiments, bupropion, hydroxybupropion, threohydroxybupropion, erythrohydroxybupropion, or a metabolite or prodrug of any of these compounds, are co-administered for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite of prodrug of any of these compounds, for five consecutive days. For example, the dextromethorphan plasma level on the fifth day (for example at 0 hours, 1 hour, 3 hours, 6 hours, or 12 hours after administration) may be at least 5 times, at least 10 times, at least 20 times, at least 40 times, at least 50 times, at least 60 times, at least 65 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for five consecutive days.

In some embodiments, bupropion, hydroxybupropion, threohydroxybupropion, erythrohydroxybupropion, or a metabolite or prodrug of any of these compounds, and dextromethorphan, are co-administered for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for six consecutive days. For example, the dextromethorphan plasma level on the sixth day (for example at 0 hours, 1 hour, 3 hours, 6 hours, or 12 hours after administration) may be at least 5 times, at least 10 times, at least 20 times, at least 30 times, at least 50 times, at least 60 times, at least 70 times, at least 75 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for six consecutive days.

In some embodiments, bupropion, hydroxybupropion, threohydroxybupropion, erythrohydroxybupropion, or a metabolite or prodrug of any of these compounds, and dextromethorphan, are co-administered for at least seven consecutive days, to a human being in need of treatment with dextromethorphan, wherein, on the seventh day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for seven consecutive days. For example, the dextromethorphan plasma level on the seventh day (for example at 0 hours, 1 hour, 3 hours, 6 hours, or 12 hours after administration) may be at least 5 times, at least 10 times, at least 20 times, at least 30 times, at least 50 times, at least 70 times, at least 80 times, at least 90 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for seven consecutive days.

In some embodiments, bupropion, hydroxybupropion, threohydroxybupropion, erythrohydroxybupropion, or a metabolite or prodrug of any of these compounds, and dextromethorphan, are co-administered for at least eight consecutive days, wherein, on the eighth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion, hydroxybupropion, threohydroxybupropion, erythrohydroxybupropion, or a metabolite or prodrug of any of these compounds, and dextromethorphan are co-administered for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for eight consecutive days. For example, the dextrorphan plasma level on the eighth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion may be administered to a human being in an amount that results in an $AUC_{0-12}$ of bupropion in the human being, on day 8, that is at least about 100 ng·hr/mL, at least about 200 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1,000 ng·hr/mL, at least about 1,200 ng·hr/mL, at least 1,600 ng·hr/mL, or up to about 15,000 ng·hr/mL.

In some embodiments, bupropion may be administered to a human being in an amount that results in a $C_{avg}$ of bupropion in the human being, on day 8, that is at least about 10 ng/mL, at least about 20 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least 120 ng/mL, or up to about 1,500 ng/mL.

In some embodiments, bupropion may be administered to a human being in an amount that results in a $C_{max}$ of bupropion in the human being, on day 8, that is at least about 10 ng/mL, at least about 20 ng/mL, at least about 50 ng/mL, at least about 90 ng/mL, at least about 100 ng/mL, at least about 110 ng/mL, at least about 120 ng/mL, at least about 130 ng/mL, at least about 140 ng/mL, at least 200 ng/mL, or up to about 1,500 ng/mL.

Some liquid compositions may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of bupropion, or any amount of bupropion in a range bounded by, or between, any of these values.

Some liquid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 180 mg to about 220 mg, about 280 mg to about 320 mg, about 200 mg, about 150 mg, or about 300 mg of bupropion, or any amount of bupropion in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of bupropion, or any amount of bupropion in a range bounded by, or between, any of these values.

Some solid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 50 mg to about 150 mg, about 180 mg to about 220 mg, about 280 mg to about 320 mg, about 200 mg, about 150 mg, or about 300 mg of bupropion, or any amount of bupropion in a range bounded by, or between, any of these values.

In some embodiments, bupropion is administered at a dose that results in a bupropion plasma level of about 0.1 µM to about 10 µM, about 0.1 µM to about 5 µM, about 0.2 µM to about 3 µM, 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, hydroxybupropion, or a prodrug of hydroxybupropion, is administered at a dose that results in a hydroxybupropion plasma level of about 0.1 µM to about 10 µM, about 0.1 µM to about 5 µM, about 0.2 µM to about 3 µM, 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, hydroxybupropion, or a prodrug of hydroxybupropion, may be administered to a human being in an amount that results in an $AUC_{0-12}$ of hydroxybupropion in the human being, on day 8, that is at least about 3,000 ng·hr/mL, at least about 7,000 ng·hr/mL, at least about 10,000 ng·hr/mL, at least about 15,000 ng·hr/mL, at least about 20,000 ng·hr/mL, at least about 30,000 ng·hr/mL, up to about 50,000 ng·hr/mL, up to about 150,000 ng·hr/mL, or any AUC in a range bounded by, or between, any of these values.

In some embodiments, bupropion, hydroxybupropion, or a prodrug of hydroxybupropion, may be administered to a human being in an amount that results in a $C_{max}$ of hydroxybupropion in the human being, on day 8, that is at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{max}$ in a range bounded by, or between, any of these values.

In some embodiments, bupropion, hydroxybupropion, or a prodrug of hydroxybupropion, may be administered to a human being in an amount that results in a $C_{avg}$ of hydroxybupropion in the human being, on day 8, that is at least about 200 ng/mL, at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{avg}$ in a range bounded by, or between, any of these values.

In some embodiments, bupropion, threohydroxybupropion, or a prodrug of threohydroxybupropion, is administered at a dose that results in a threohydroxybupropion plasma level of about 0.1 µM to about 10 µM, about 0.1 µM to about 5 µM, about 0.2 µM to about 3 µM, 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, threohydroxybupropion, or a prodrug of threohydroxybupropion, may be administered to a human being in an amount that results in an $AUC_{0-12}$ of threohydroxybupropion in the human being, on day 8, that is at least about 1,000 ng·hr/mL, at least about 2,000 ng·hr/mL, at least about 4,000 ng·hr/mL, at least about 5,000 ng·hr/mL, at least about 8,000 ng·hr/mL, up to about 10,000 ng·hr/mL, up to about 40,000 ng·hr/mL, or any AUC in a range bounded by, or between, any of these values.

In some embodiments, bupropion, threohydroxybupropion, or a prodrug of threohydroxybupropion, may be administered to a human being in an amount that results in a $C_{max}$ of threohydroxybupropion in the human being, on day 8, that is at least about 100 ng/mL, at least about 200 ng/mL, at least about 400 ng/mL, at least about 500 ng/mL, at least about 600 ng/mL, at least about 800 ng/mL, up to about 2,000 ng/mL, up to about 10,000 ng/mL, or any $C_{max}$ in a range bounded by, or between, any of these values.

In some embodiments, bupropion, threohydroxybupropion, or a prodrug of threohydroxybupropion, may be administered to a human being in an amount that results in a $C_{avg}$ of threohydroxybupropion in the human being, on day 8, that is at least about 100 ng/mL, at least about 300 ng/mL, at least about 400 ng/mL, at least about 600 ng/mL, at least about 800 ng/mL, up to about 2,000 ng/mL, up to about 10,000 ng/mL, or any $C_{avg}$ in a range bounded by, or between, any of these values.

In some embodiments, bupropion, erythrohydroxybupropion, or a prodrug of erythrohydroxybupropion, is administered at a dose that results in an erythrohydroxybupropion plasma level of about 0.1 µM to about 10 µM, about 0.1 µM to about 5 µM, about 0.2 µM to about 3 µM, 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, erythrohydroxybupropion, or a prodrug of erythrohydroxybupropion, may be administered to a human being in an amount that results in an $AUC_{0-12}$ of erythrohydroxybupropion in the human being, on day 8, that is at least about 200 ng·hr/mL, at least about 400 ng·hr/mL, at least about 700 ng·hr/mL, at least about 1,000 ng·hr/mL, at least about 1,500 ng·hr/mL, at least about 3,000 ng·hr/mL, up to about 5,000 ng·hr/mL, up to about 30,000 ng·hr/mL, or any plasma level in a range bounded by, or between, any of these values.

In some embodiments, bupropion, erythrohydroxybupropion, or a prodrug of erythrohydroxybupropion, may be administered to a human being in an amount that results in a $C_{max}$ of erythrohydroxybupropion in the human being, on day 8, that is at least about 30 ng/mL, at least about 60 ng/mL, at least about 90 ng/mL, at least about 100 ng/mL, at least about 150 ng/mL, at least about 200 ng/mL, at least about 300 ng/mL, up to about 1,000 ng/mL, or any $C_{max}$ in a range bounded by, or between, any of these values.

In some embodiments, bupropion, erythrohydroxybupropion, or a prodrug of erythrohydroxybupropion, may be administered to a human being in an amount that results in a $C_{avg}$ of erythrohydroxybupropion in the human being, on day 8, that is at least about 20 ng/mL, at least about 30 ng/mL, at least about 50 ng/mL, at least about 80 ng/mL, at least about 90 ng/mL, at least about 100 ng/mL, at least about 150 ng/mL, at least about 200 ng/mL, at least about 300 ng/mL, up to about 1,000 ng/mL, up to about 5,000 ng/mL, or any $C_{avg}$ in a range bounded by, or between, any of these values.

For compositions comprising both dextromethorphan and bupropion, some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), about 40% (w/v) to about 50% (w/v) of dextromethorphan and bupropion combined, or any amount in a range bounded by, or between, any of these values. Some solid compositions may comprise at least about 5% (w/w), at least about 10% (w/w), at least about 20% (w/w), at least about 50% (w/w), at least about 70% (w/w), at least about 80%, at least about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), about 80% (w/w) to about 90% (w/w) of dextromethorphan and bupropion combined, or any amount in a range bounded by, or between, any of these values. In some embodiments, the weight ratio of dextromethorphan to bupropion in a single composition or dosage form may be about 0.1 to about 2, about 0.2 to about 1, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values.

A therapeutically effective amount of a therapeutic compound may vary depending upon the circumstances. For example, a daily dose of dextromethorphan may in some instances range from about 0.1 mg to about 1000 mg, about 40 mg to about 1000 mg, about 20 mg to about 600 mg, about 60 mg to about 700 mg, about 100 mg to about 400 mg, about 15 mg to about 20 mg, about 20 mg to about 25 mg, about 25 mg to about 30 mg, about 30 mg to about 35 mg, about 35 mg to about 40 mg, about 40 mg to about 45 mg, about 45 mg to about 50 mg, about 50 mg to about 55 mg, about 55 mg to about 60 mg, about 20 mg to about 60 mg, about 60 mg to about 100 mg, about 100 mg to about 200 mg, about 100 mg to about 140 mg, about 160 mg to about 200 mg, about 200 mg to about 300 mg, about 220 mg to about 260 mg, about 300 mg to about 400 mg, about 340 mg to about 380 mg, about 400 mg to about 500 mg, about 500 mg to about 600 mg, about 15 mg, about 30 mg, about 60 mg, about 120 mg, about 180 mg, about 240 mg, about 360 mg, or any daily dose in a range bounded by, or between, any of these values. Dextromethorphan may be administered once daily; or twice daily or every 12 hours, three times daily, four times daily, or six times daily in an amount that is about half, one third, one quarter, or one sixth, respectively, of the daily dose.

A daily dose of bupropion, may in some instances range from about 10 mg to about 1000 mg, about 50 mg to about 600 mg, about 100 mg to about 2000 mg, about 50 mg to about 100 mg, about 70 mg to about 95 mg, about 100 mg to about 200 mg, about 105 mg to about 200 mg, about 100 mg to about 150 mg, about 150 mg to about 300 mg, about 150 mg to about 200 mg, about 200 mg to about 250 mg, about 250 mg to about 300 mg, about 200 mg about 300 mg, about 300 mg to about 400 mg, about 400 mg to about 500 mg, about 400 mg to about 600 mg, about 360 mg to about 440 mg, about 560 mg to about 640 mg, or about 500 mg to about 600 mg, about 100 mg, about 150 mg, about 200 mg, about 300 mg, about 400 mg, about 600 mg, or any daily dose in a range bounded by, or between, any of these values. Bupropion may be administered once daily; or twice daily or every 12 hours, or three times daily in an amount that is about half or one third, respectively, of the daily dose.

In some embodiments: 1) about 50 mg/day to about 100 mg/day, about 100 mg/day to about 150 mg/day, about 150 mg/day to about 300 mg/day, about 150 mg/day to about 200 mg/day, about 200 mg/day to about 250 mg/day, about 250 mg/day to about 300 mg/day of bupropion, or about 300 mg/day to about 500 mg/day of bupropion; and/or 2) about 15 mg/day to about 60 mg/day, about 15 mg/day to about 30 mg/day, about 30 mg/day to about 45 mg/day, about 45 mg/day to about 60 mg/day, about 60 mg/day to about 100 mg/day, about 80 mg/day to about 110 mg/day, about 100 mg/day to about 150 mg/day, or about 100 mg/day to about 300 mg/day of dextromethorphan, are administered to a human being in need thereof.

In some embodiments, about 150 mg/day of bupropion and about 30 mg/day of dextromethorphan, about 150 mg/day of bupropion and about 60 mg/day of dextromethorphan, about 150 mg/day of bupropion and about 90 mg/day of dextromethorphan, about 150 mg/day of bupropion and about 120 mg/day of dextromethorphan, about 200 mg/day of bupropion and about 30 mg/day of dextromethorphan, about 200 mg/day of bupropion and about 60 mg/day of dextromethorphan, about 200 mg/day of bupropion and about 90 mg/day of dextromethorphan, about 200 mg/day of bupropion and about 120 mg/day of dextromethorphan, about 300 mg/day of bupropion and about 30 mg/day of dextromethorphan, about 300 mg/day of bupropion and about 60 mg/day of dextromethorphan, about 300 mg/day of bupropion and about 90 mg/day of dextromethorphan, or about 300 mg/day of bupropion and about 120 mg/day of dextromethorphan is administered to the human being.

In some embodiments, about 100 mg/day of bupropion and about 15 mg/day of dextromethorphan is administered to the human being for 1, 2, or 3 days, followed by about 200 mg/day of bupropion and about 30 mg/day of dextromethorphan. In some embodiments, about 100 mg/day of bupropion and about 30 mg/day of dextromethorphan is administered to the human being for 1, 2, or 3 days, followed by about 200 mg/day of bupropion and about 60 mg/day of dextromethorphan.

In some embodiments, about 75 mg/day of bupropion and about 15 mg/day of dextromethorphan is administered to the human being for 1, 2, or 3 days, followed by about 150 mg/day of bupropion and about 30 mg/day of dextromethorphan. In some embodiments, about 75 mg/day of bupropion and about 30 mg/day of dextromethorphan is administered to the human being for 1, 2, or 3 days, followed by about 150 mg/day of bupropion and about 60 mg/day of dextromethorphan.

An antidepressant compound, such as bupropion, may be administered for as long as needed to treat a neurological condition, such as pain, depression or cough. In some embodiments, an antidepressant compound, such as bupropion, and dextromethorphan are administered at least once a day, such as once daily or twice daily, for at least 1 day, at least 3 days, at least 5 days, at least 7 days, at least 8 days, at least 14 days, at least 30 days, at least 60 days, at least 90 days, at least 180 days, at least 365 days, or longer.

Therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

Tablets, troches, pills, capsules and the like may also contain one or more of the following: a binder such as gum tragacanth, acacia, corn starch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Therapeutic compounds may be formulated for parental or intraperitoneal administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

Specifically Contemplated Embodiments

The following are examples of embodiments that are specifically contemplated by the inventor:

Embodiment 1

A method of treating pain or a neurological disorder comprising administering a therapeutically effective amount of dextromethorphan and a therapeutically effective amount of an antidepressant compound, to a person in need thereof.

Embodiment 2

A method of treating pain comprising administering a combination of an antidepressant compound and dextromethorphan to a human being in need thereof.

Embodiment 3

A method of enhancing the pain relieving properties of dextromethorphan, comprising co-administering dextromethorphan and an antidepressant compound.

Embodiment 4

A method of increasing dextromethorphan plasma levels in a human being that is an extensive metabolizer of dextromethorphan, comprising co-administering an antidepressant compound to the human being receiving a treatment that includes administration of dextromethorphan.

Embodiment 5

A method of inhibiting the metabolism of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 6

A method of increasing the metabolic lifetime of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 7

A method of correcting extensive metabolism of dextromethorphan, comprising administering an antidepressant compound to a human being in need thereof.

Embodiment 8

A method of improving pain relieving properties of dextromethorphan comprising administering an antidepressant compound in conjunction with administration of dextromethorphan to a human being in need of treatment for pain.

Embodiment 9

A method of improving antitussive properties of dextromethorphan comprising administering an antidepressant compound in conjunction with administration of dextromethorphan to a human being in need of treatment for cough.

Embodiment 10

A method of treating cough comprising administering a combination of an antidepressant compound and dextromethorphan to a human being in need thereof.

Embodiment 11

A method of improving a therapeutic property of dextromethorphan comprising administering an antidepressant compound in conjunction with administration of dextromethorphan to a human being in need of treatment for a neurological disorder.

Embodiment 12

A method of treating a neurological disorder comprising administering a combination of an antidepressant compound and dextromethorphan to a human being in need thereof.

Embodiment 13

A method of treating a neurological disorder comprising administering an antidepressant compound and dextromethorphan to a human being in need thereof, wherein the human being is an extensive metabolizer of dextromethorphan.

Embodiment 14

The method of embodiment 1, 2, 3, 4, 5, 6, 7, 8, 9, 10, 11, 12, or 13, wherein the dextromethorphan and the antidepressant compound are administered in separate dosage forms.

Embodiment 15

A pharmaceutical composition comprising a therapeutically effective amount of dextromethorphan, a therapeutically effective amount of an antidepressant compound, and a pharmaceutically acceptable excipient.

Embodiment 16

An oral dosage form comprising at least 20 mg of dextromethorphan and an effective amount of an antidepressant compound to inhibit the metabolism of dextromethorphan in a human being that is an extensive metabolizer of dextromethorphan.

Embodiment 17

The oral dosage form of embodiment 16, wherein about 30 mg to about 350 mg of dextromethorphan is present in the dosage form.

Embodiment 18

The oral dosage form of embodiment 16 or 17, wherein about 100 mg to about 400 mg of bupropion is present in the dosage form.

Embodiment 19

The oral dosage form of any of embodiments 16, 17, or 18, comprising an amount of bupropion that results in a bupropion plasma level of about 0.1 µM to about 10 µM when the oral dosage form is administered to a human being.

Embodiment 20

The oral dosage form of embodiment 19, comprising an amount of bupropion that results in a bupropion plasma level of about 0.1 µM to about 2 µM when the oral dosage form is administered to a human being.

Embodiment 21

The method of embodiment 1, 2, 3, 4, 5, 6, 7, 8, 9, 10, 11, 12, or 13, wherein bupropion is administered at a dose that results in a bupropion plasma level of about 0.1 µM to about 10 µM.

Embodiment 22

The method of embodiment 21, wherein bupropion is administered at a dose that results in a bupropion plasma level of about 0.3 µM to about 1 µM.

Embodiment 23

The method, composition, or dosage form of any of embodiments 1, 2, 3, 4, 5, 6, 7, 8, 9, 10, 11, 12, 13, 14, 15, 16, or 17, wherein the antidepressant compound is bupropion or a metabolite thereof.

Embodiment 24

The method, composition, or dosage form of any of embodiments 1, 2, 3, 4, 5, 6, 7, 8, 9, 10, 11, 12, 13, 14, 15, 16, or 17, wherein the antidepressant compound is bupropion.

Embodiment 25

The method, composition, or dosage form of embodiment 1, 2, 3, 4, 5, 6, 7, 8, 9, 10, 11, 12, 13, 14, 15, 16, or 17, wherein the antidepressant compound is clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, or a pharmaceutically acceptable salt thereof

Embodiment 26

The method of embodiment 1, 2, 3, 4, 5, 6, 7, 8, 11, 12, 13, 14, 21, 22, 23, 24, or 25, wherein dextromethorphan is administered to the human being for the treatment of cough.

Embodiment 27

A method of treating a neurological disorder comprising administering about 150 mg/day to about 300 mg/day of bupropion and about 30 mg/day to about 120 mg/day of dextromethorphan to a human being in need thereof.

Embodiment 28

A method of treating a neurological disorder comprising administering bupropion and dextromethorphan to a human being in need thereof, wherein the bupropion and dextromethorphan are administered at least once a day for at least 8 days.

Embodiment 29

The method of embodiment 1, 2, 3, 4, 5, 6, 7, 8, 9, 10, 11, 12, 13, 14, 21, 22, 23, 24, 25, 26, or 27, wherein bupropion is administered to the human being at least daily for at least 8 days.

Embodiment 30

The method of embodiment 1, 2, 3, 4, 5, 6, 7, 8, 9, 10, 11, 12, 13, 14, 21, 22, 23, 24, 25, 26, 27, or 28, wherein dextromethorphan is administered to the human being at least daily for at least 8 days.

Embodiment 31

The method of embodiment 28, 29, or 30, wherein bupropion is administered in an amount that results in a plasma concentration of dextromethorphan in the human being, on day 8, that is at least 10 times the plasma concentration of the same amount of dextromethorphan administered without bupropion.

Embodiment 32

The method of embodiment 28, 29, 30, or 31, wherein bupropion is administered in an amount that results in an $AUC_{0-12}$ of hydroxybupropion, on day 8, that is at least about 3000 ng·hr/mL.

Embodiment 33

The method of embodiment 28, 29, 30, 31, or 32, wherein bupropion is administered in an amount that results in an $AUC_{0-12}$ of erythrohydroxybupropion, on day 8, that is at least about 400 ng·hr/mL.

Embodiment 34

The method of embodiment 28, 29, 30, 31, 32, or 33, wherein bupropion is administered in an amount that results in an $AUC_{0-12}$ of threohydroxybupropion, on day 8, that is at least about 2000 ng·hr/mL.

Embodiment 35

The method, composition, or dosage form of embodiment 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, or 34, wherein the weight ratio of dextromethorphan to bupropion is about 0.1 to about 0.5.

Embodiment 36

The method of embodiment 27, 28, 29, 30, 31, 32, 33, 34, or 35, wherein the human being is an extensive metabolizer of dextromethorphan.

Embodiment 37

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 30 mg/day of dextromethorphan is administered to the human being.

Embodiment 38

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 60 mg/day of dextromethorphan is administered to the human being.

Embodiment 39

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 30 mg/day of dextromethorphan is administered to the human being.

Embodiment 40

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 15 mg/day of dextromethorphan is administered to the human being for about 1 to about 3 days, followed by about 200 mg/day of bupropion and about 30 mg/day of dextromethorphan.

Embodiment 41

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 60 mg/day of dextromethorphan is administered to the human being.

Embodiment 42

The method of embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 30 mg/day of dextromethorphan is administered to the human being for about 1 to about 3 days, followed by about 200 mg/day of bupropion and about 60 mg/day of dextromethorphan.

Embodiment 43

The method of embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, or 42, wherein dextromethorphan is administered to the human being for the treatment of pain.

Embodiment 44

The method of embodiment 43, wherein the pain comprises postoperative pain, cancer pain, arthritic pain, lumbosacral pain, musculoskeletal pain, central multiple sclerosis pain, nociceptive pain, or neuropathic pain.

Embodiment 45

The method of embodiment 43, wherein the pain comprises musculoskeletal pain, neuropathic pain, cancer-related pain, acute pain, or nociceptive pain.

Embodiment 46

The method of embodiment 43, wherein the pain comprises postoperative pain.

Embodiment 47

The method of embodiment 43, wherein the pain comprises cancer pain.

Embodiment 48

The method of embodiment 43, wherein the pain comprises arthritic pain.

Embodiment 49

The method of embodiment 43, wherein the pain comprises lumbosacral pain.

Embodiment 50

The method of embodiment 43, wherein the pain comprises musculoskeletal pain.

Embodiment 51

The method of embodiment 43, wherein the pain comprises neuropathic pain.

Embodiment 52

The method of embodiment 43, wherein the pain comprises nociceptive pain.

Embodiment 53

The method of embodiment 43, wherein the pain comprises chronic musculoskeletal pain.

Embodiment 54

The method of embodiment 43, wherein the pain is associated with rheumatoid arthritis.

Embodiment 55

The method of embodiment 43, wherein the pain is associated with juvenile rheumatoid arthritis.

Embodiment 56

The method of embodiment 43, wherein the pain is associated with osteoarthritis.

Embodiment 57

The method of embodiment 43, wherein the pain is associated with an axial spondyloarthritis.

Embodiment 58

The method of embodiment 43, wherein the pain is associated with ankylosing spondylitis.

Embodiment 59

The method of embodiment 43, wherein the pain is associated with diabetic peripheral neuropathy.

Embodiment 60

The method of embodiment 43, wherein the pain is associated with post-herpetic neuralgia.

Embodiment 61

The method of embodiment 43, wherein the pain is associated with trigeminal neuralgia.

Embodiment 62

The method of embodiment 43, wherein the pain is associated with monoradiculopathies.

Embodiment 63

The method of embodiment 43, wherein the pain is associated with phantom limb pain.

Embodiment 64

The method of embodiment 43, wherein the pain is associated with central pain.

Embodiment 65

The method of embodiment 43, wherein the pain comprises cancer-related pain.

Embodiment 66

The method of embodiment 43, wherein the pain is associated with lumbar nerve root compression.

Embodiment 67

The method of embodiment 43, wherein the pain is associated with spinal cord injury.

Embodiment 68

The method of embodiment 43, wherein the pain is associated with post-stroke pain.

Embodiment 69

The method of embodiment 43, wherein the pain is associated with central multiple sclerosis pain.

Embodiment 70

The method of embodiment 43, wherein the pain is associated with HIV-associated neuropathy.

Embodiment 71

The method of embodiment 43, wherein the pain is associated with radio-therapy associated neuropathy.

Embodiment 72

The method of embodiment 43, wherein the pain is associated with chemo-therapy associated neuropathy.

Embodiment 73

The method of embodiment 43, wherein the pain comprises dental pain.

Embodiment 74

The method of embodiment 43, wherein the pain is associated with primary dysmenorrhea.

Embodiment 75

The method of embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, wherein 90 mg/day of dextromethorphan is administered to the human being.

Embodiment 76

The method of embodiment 75, wherein 45 mg of dextromethorphan is administered twice a day to the human being.

Embodiment 77

The method of embodiment 75 or 76, wherein 150 mg/day of bupropion is administered to the human being.

Embodiment 78

The method of embodiment 75 or 76, wherein 180 mg/day of bupropion is administered to the human being.

Embodiment 79

The method of embodiment 75 or 76, wherein 200 mg/day of bupropion is administered to the human being.

Embodiment 80

The method of embodiment 75 or 76, wherein 300 mg/day of bupropion is administered to the human being.

U.S. Provisional Application No. 61/900,354 is incorporated by reference herein in its entirety. PCT Application No. PCT/US2014/64184 is incorporated by reference herein in its entirety. U.S. Patent Publication No. 2015/0126543 is incorporated by reference herein in its entirety.

EXAMPLES

Example 1

Fifteen human subjects were randomized into one of two treatment groups receiving either dextromethorphan (DM) alone, or DM in combination with bupropion, as shown in Table 1 below.

TABLE 1

Study Design

| Group | Dose Levels Bupropion/DM | Dosing Regimen | Duration | Total Subjects |
|---|---|---|---|---|
| A | 0 mg/60 mg | DM: Twice daily, Days 1-8 | Days 1-8 | 8 |
| B | 150 mg/60 mg | Bupropion: Once daily, Days 1-3; Twice daily, Days 4-8 DM: Twice daily, Days 1-8 | Days 1-8 | 7 |

All subjects were extensive, including ultra-rapid, metabolizers of dextromethorphan as determined by CYP2D6 genetic testing. Dextromethorphan was dosed at 12-hour intervals on Days 1-8, with a final morning dose on Day 8. Bupropion was dosed once daily on Days 1-3, and at 12-hour intervals thereafter, with a final morning dose on Day 8.

Plasma samples were collected for concentration analysis of dextromethorphan, total dextrorphan, bupropion, hydroxybupropion, erythrohydroxybupropion, and threohydroxybupropion on days 1 and 8. Plasma samples for determination of trough concentrations of dextromethorphan were obtained approximately 12 hours after dosing on days 1, 5, 6, and 8.

Concentrations of dextromethorphan, total dextrorphan (unconjugated and glucuronide forms), bupropion, hydroxybupropion, erythrohydroxybupropion, and threohydroxybupropion, were determined using LC-MS/MS. Pharmacokinetic parameters were calculated.

Phenotypic determination of dextromethorphan metabolizer status was performed by calculating the dextromethorphan/dextrorphan metabolic ratio as described in Jurica et al. Journal of Clinical Pharmacy and Therapeutics, 2012, 37, 486-490. Plasma concentrations of dextromethorphan and dextrorphan 3 hours after dosing were used, with a dextromethorphan/dextrorphan ratio of 0.3 or greater indicating a poor metabolizer phenotype.

Results

Plasma concentrations of dextromethorphan were significantly increased with bupropion administration, as illustrated in FIG. 1 and Table 2.

TABLE 2

Mean Day 8 Dextromethorphan Plasma Concentrations (ng/mL)

| Time (hours) | Dextromethorphan (Group A) | Dextromethorphan + Bupropion (Group B) |
|---|---|---|
| 0 | 1.2 | 110.6 |
| 1 | 2.4 | 129.3 |
| 2 | 3.6 | 153.9 |
| 3 | 3.6 | 151.6 |
| 4 | 3.3 | 149.1 |
| 6 | 2.5 | 150.0 |
| 8 | 1.9 | 144.4 |
| 12 | 1.1 | 119.3 |
| 24 | 0.4 | 95.3 |
| 36 | 0.1 | 69.0 |

Figure 2:
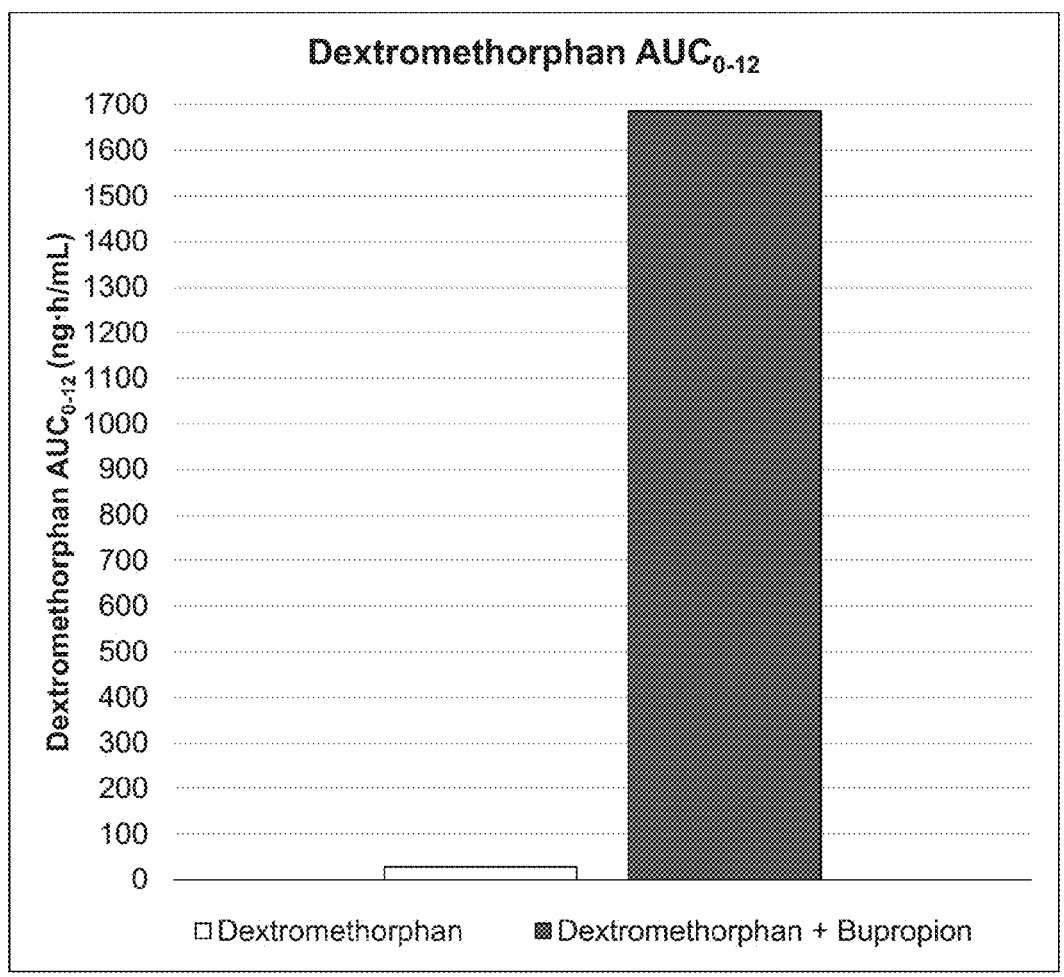
FIG. 2 depicts mean $AUC_{0-12}$ of dextromethorphan on Day 8 for subjects administered dextromethorphan alone or dextromethorphan and bupropion.
Figure 3:
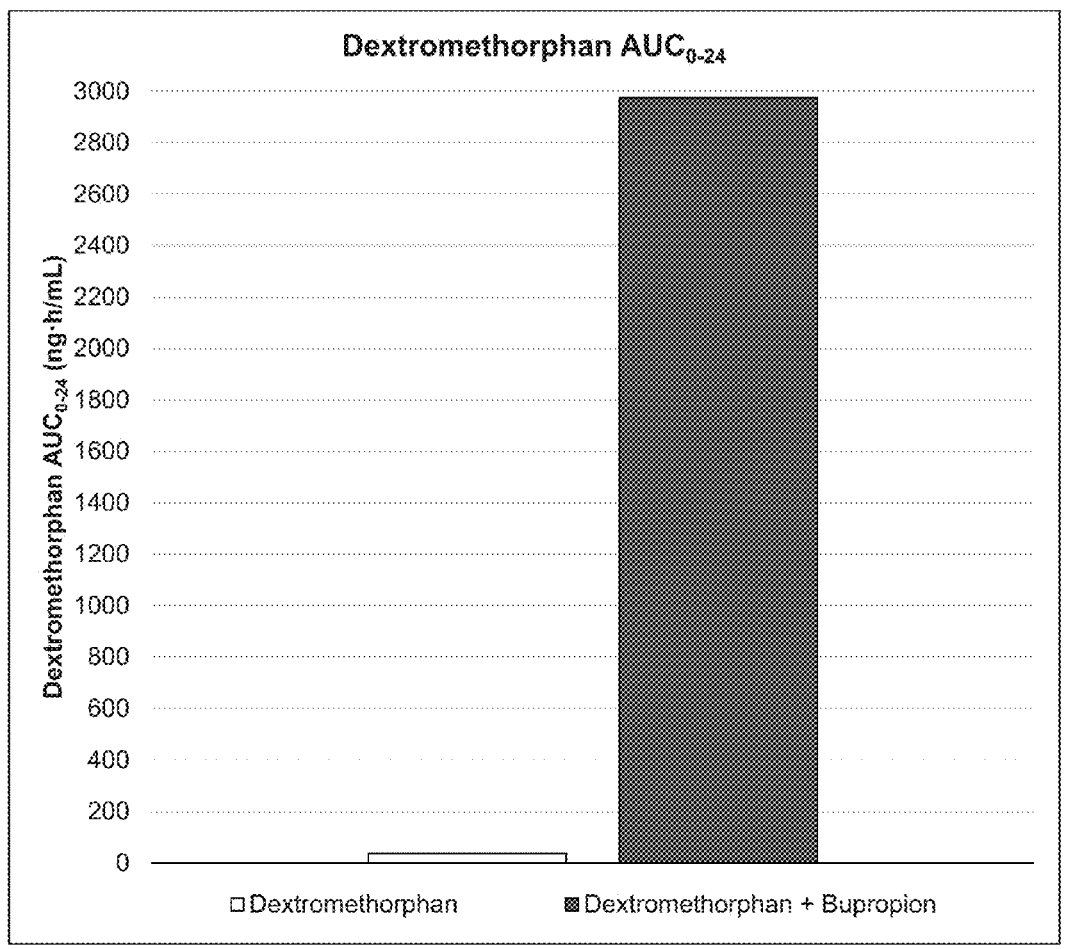
FIG. 3 depicts mean $AUC_{0-24}$ of dextromethorphan on Day 8 for subjects administered dextromethorphan alone or dextromethorphan and bupropion.
Figure 4:
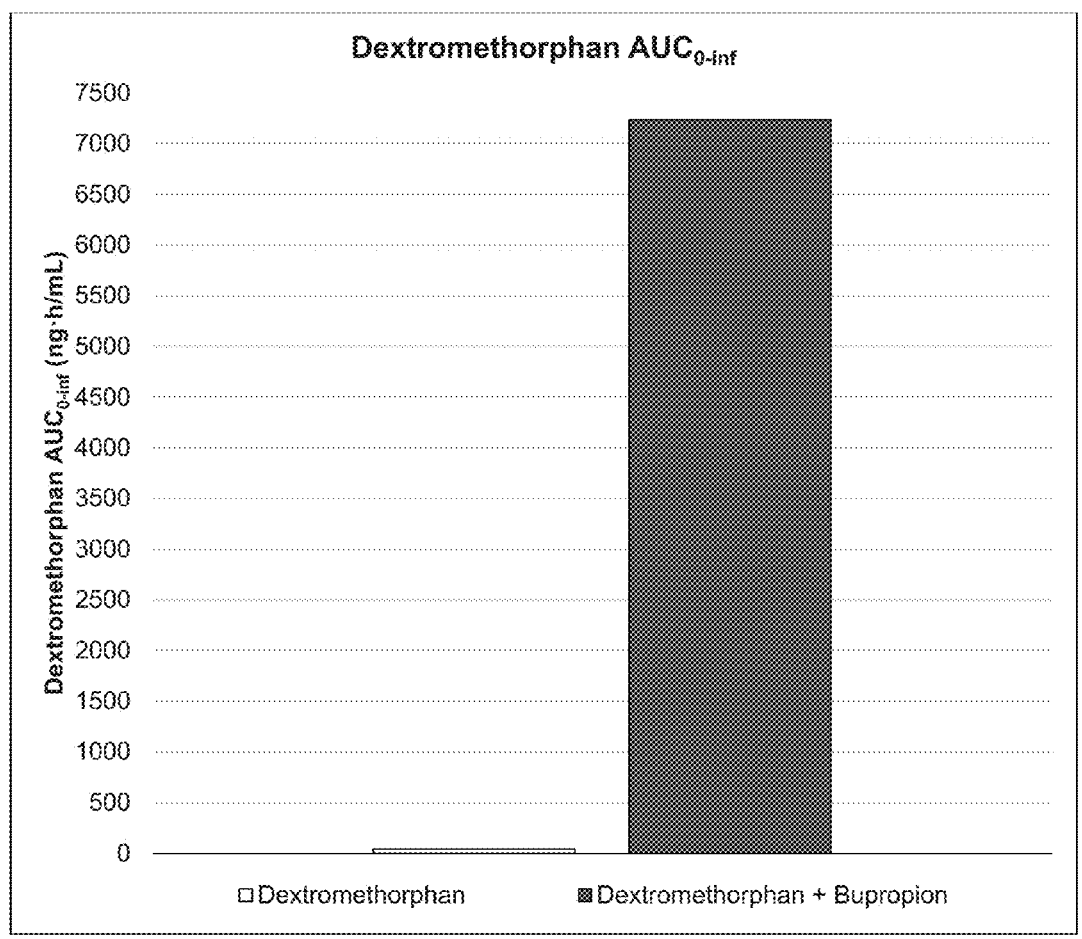
FIG. 4 depicts mean $AUC_{0-inf}$ of dextromethorphan on Day 8 for subjects administered dextromethorphan alone or dextromethorphan and bupropion.
Figure 5:
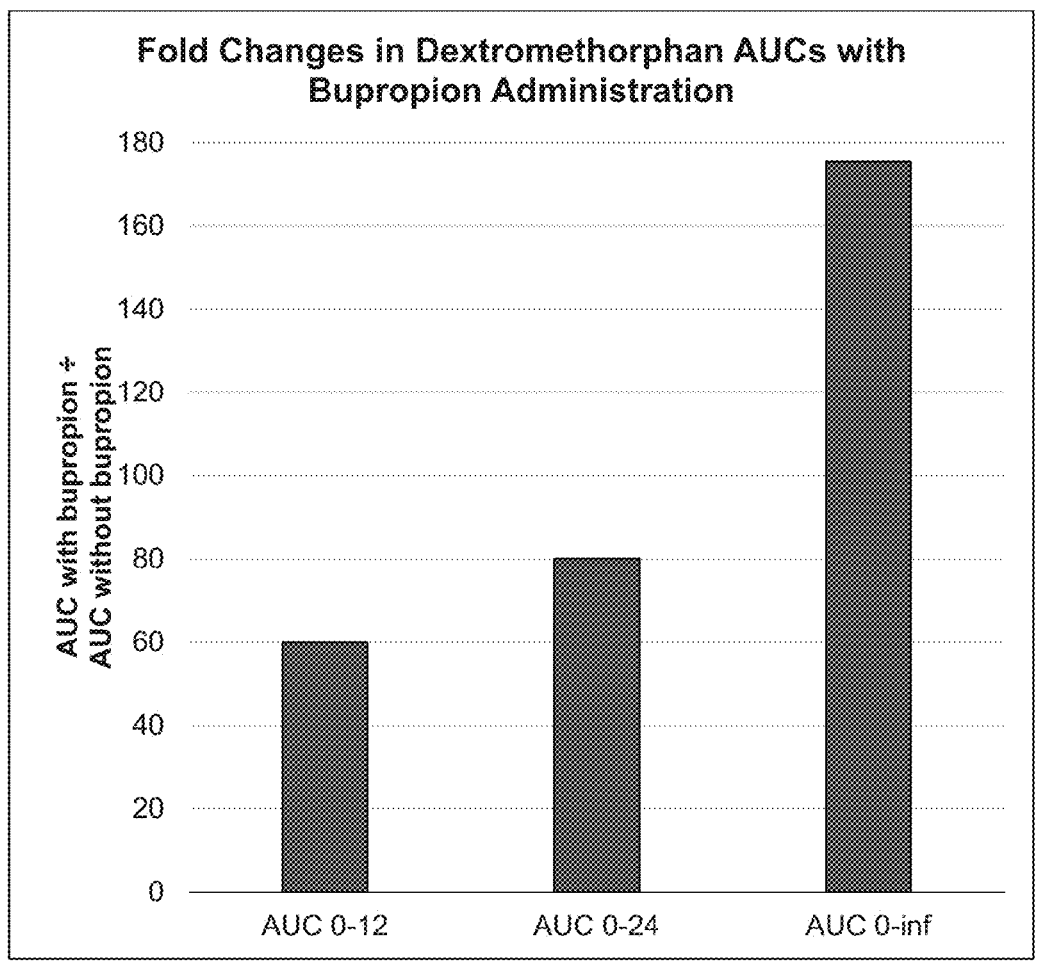
FIG. 5 depicts the fold changes in AUCs of dextromethorphan on Day 8 for subjects administered dextromethorphan alone as compared to dextromethorphan and bupropion.
Figure 6:
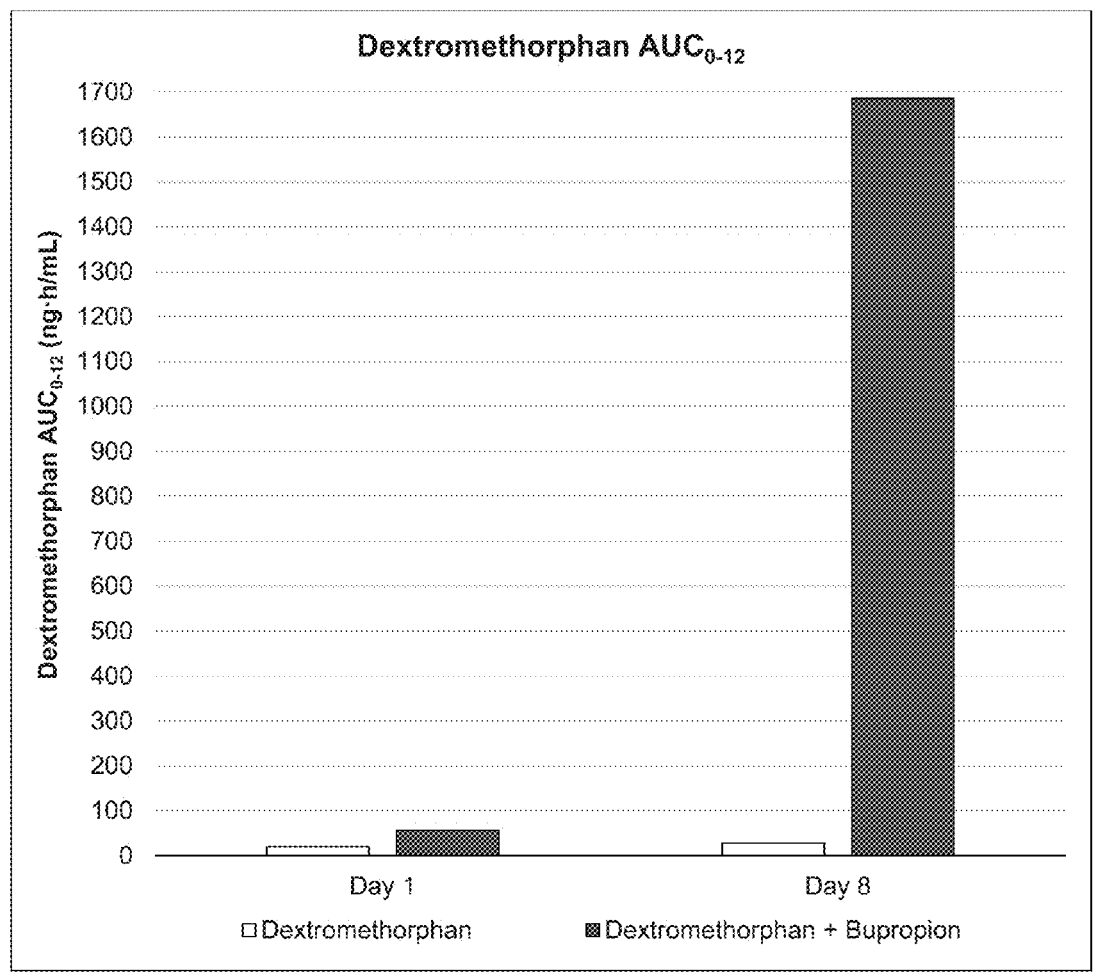
FIG. 6 depicts mean $AUC_{0-12}$ of dextromethorphan on Day 1 and Day 8 for subjects administered dextromethorphan alone or dextromethorphan and bupropion.

The AUC of dextromethorphan was significantly increased with administration of bupropion as show in FIGS. 2-4. As shown in FIG. 5, administration of bupropion with dextromethorphan resulted in an approximately 60-fold, 80-fold, and 175-fold increase in mean dextromethorphan $AUC_{0-12}$, $AUC_{0-24}$, and $AUC_{0-inf}$, respectively on Day 8 as compared to administration of dextromethorphan alone. As shown in FIG. 6, the increase in dextromethorphan AUC occurred as early as Day 1 (an approximate 3-fold increase in $AUC_{0-12}$).

Figure 7:
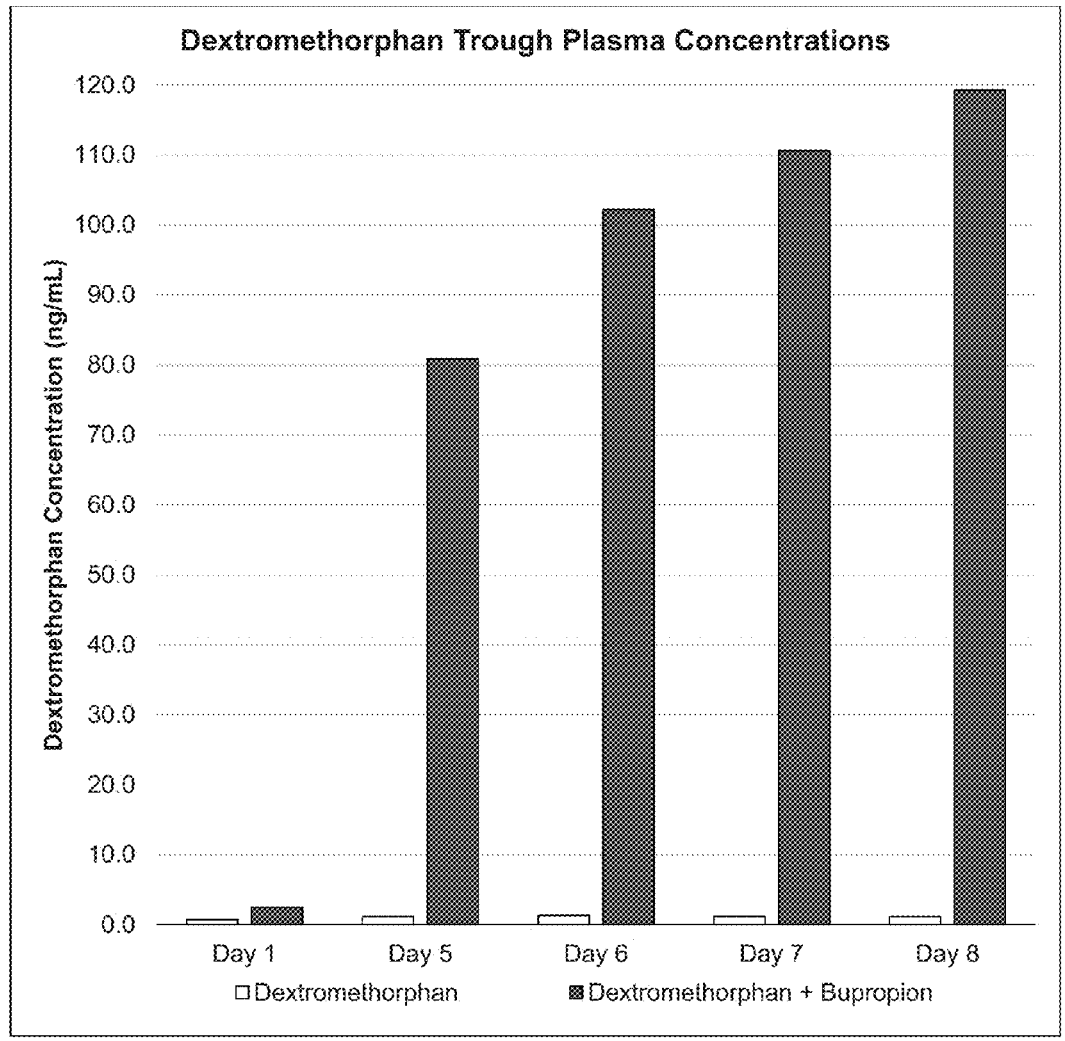
FIG. 7 depicts mean dextromethorphan trough plasma concentrations for subjects administered dextromethorphan alone or dextromethorphan and bupropion.

Trough plasma concentrations of dextromethorphan were significantly increased with administration of bupropion as illustrated in FIG. 7 and Table 3. Administration of bupropion with dextromethorphan resulted in an approximately 105-fold increase in mean trough plasma concentration of dextromethorphan on Day 8 as compared to administration of dextromethorphan alone.

Figure 8:
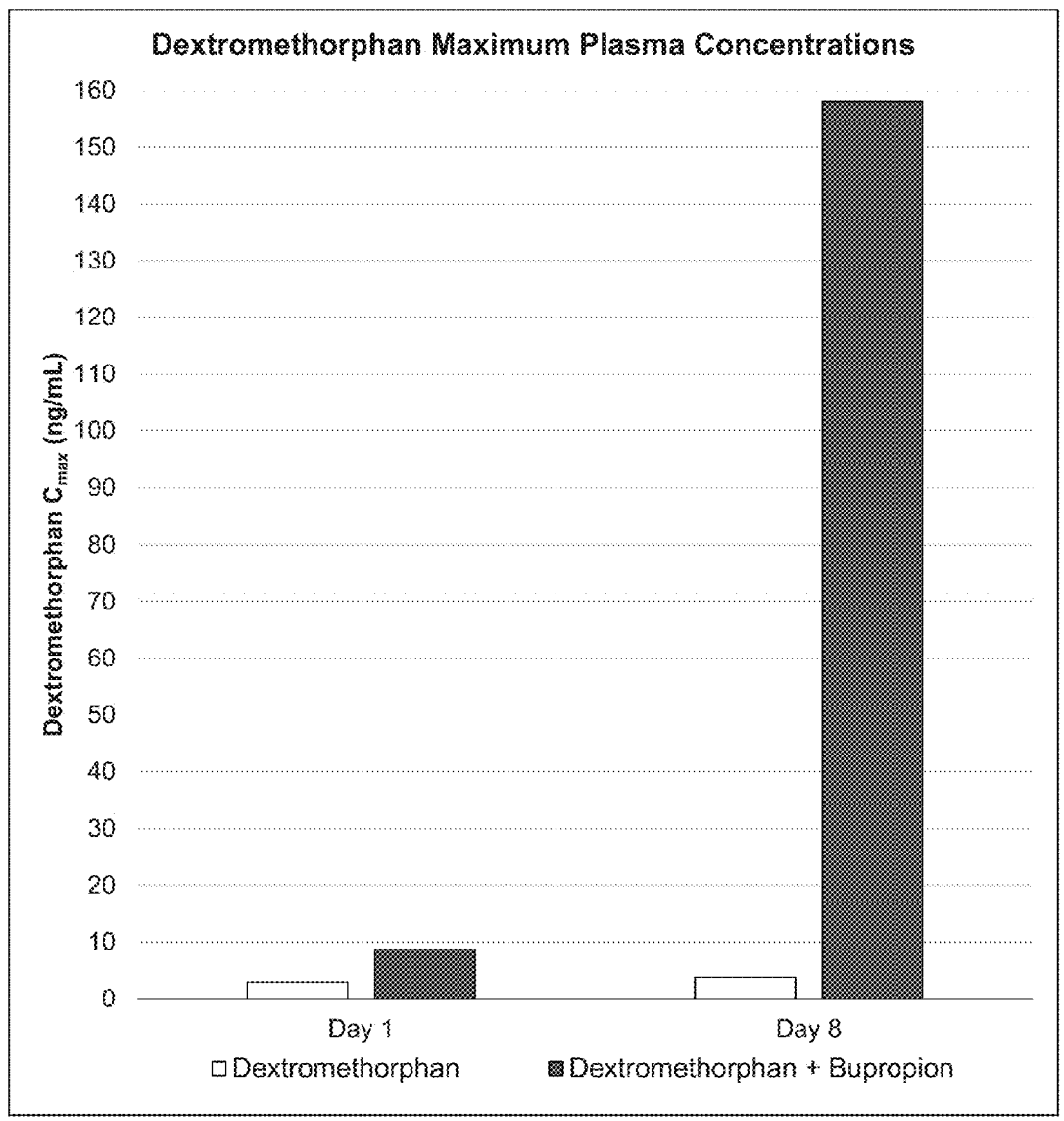
FIG. 8 depicts mean dextromethorphan maximum plasma concentrations on Day 1 and Day 8 for subjects administered dextromethorphan alone or dextromethorphan and bupropion.

Mean average plasma concentrations ($C_{avg}$) of dextromethorphan on Day 8 increased approximately 60-fold with bupropion administration as compared to administration of dextromethorphan alone. Maximum mean plasma concentrations ($C_{max}$) were also significantly increased as illustrated in FIG. 8.

TABLE 3

Mean Trough Dextromethorphan Plasma Concentrations (ng/mL)

| | Dextromethorphan (Group A) | Dextromethorphan + Bupropion (Group B) | Fold Change |
|---|---|---|---|
| Day 1 | 0.7 | 2.5 | 3.5 |
| Day 5 | 1.2 | 80.9 | 70 |
| Day 6 | 1.3 | 102.2 | 78 |
| Day 7 | 1.2 | 110.6 | 94 |
| Day 8 | 1.1 | 119.3 | 105 |

The $T_{max}$ and elimination half life ($T_{1/2\ el}$) of dextromethorphan were significantly increased with administration of bupropion on Day 8. The increase of $T_{1/2\ el}$ shows that the metabolic lifetime of dextromethorphan was increased. Administration of bupropion with dextromethorphan resulted in a mean $T_{max}$ of 3.6 hours, compared to 2.3 hours for dextromethorphan alone. Administration of bupropion with dextromethorphan resulted in a mean $T_{1/2\ el}$ of 27.7 hours, compared to 6.6 hours for dextromethorphan alone.

Figure 9:
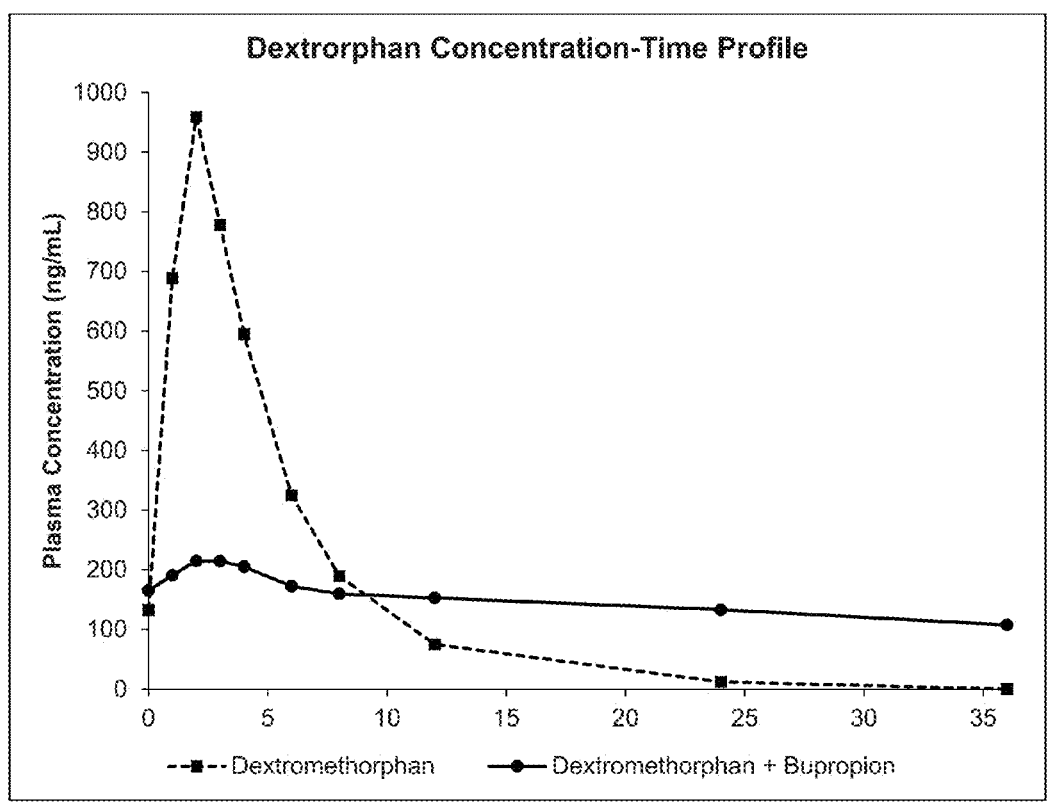
FIG. 9 is a plot of the mean plasma concentrations of dextrorphan over time after dosing on Day 8 for subjects administered dextromethorphan alone or dextromethorphan and bupropion.

Plasma concentrations of dextrorphan were significantly decreased with bupropion administration, as illustrated in FIG. 9 and Table 4.

TABLE 4

Mean Day 8 Dextrorphan Plasma Concentrations (ng/mL)

| Time (hours) | Dextromethorphan (Group A) | Dextromethorphan + Bupropion (Group B) |
|---|---|---|
| 0 | 132.4 | 165.3 |
| 1 | 688.9 | 190.7 |
| 2 | 959.1 | 214.9 |
| 3 | 778.1 | 214.4 |
| 4 | 594.9 | 205.1 |
| 6 | 324.7 | 172.5 |
| 8 | 189.6 | 159.6 |
| 12 | 74.8 | 152.8 |
| 24 | 12.2 | 133.0 |
| 36 | 0.1 | 107.6 |

Figure 10:
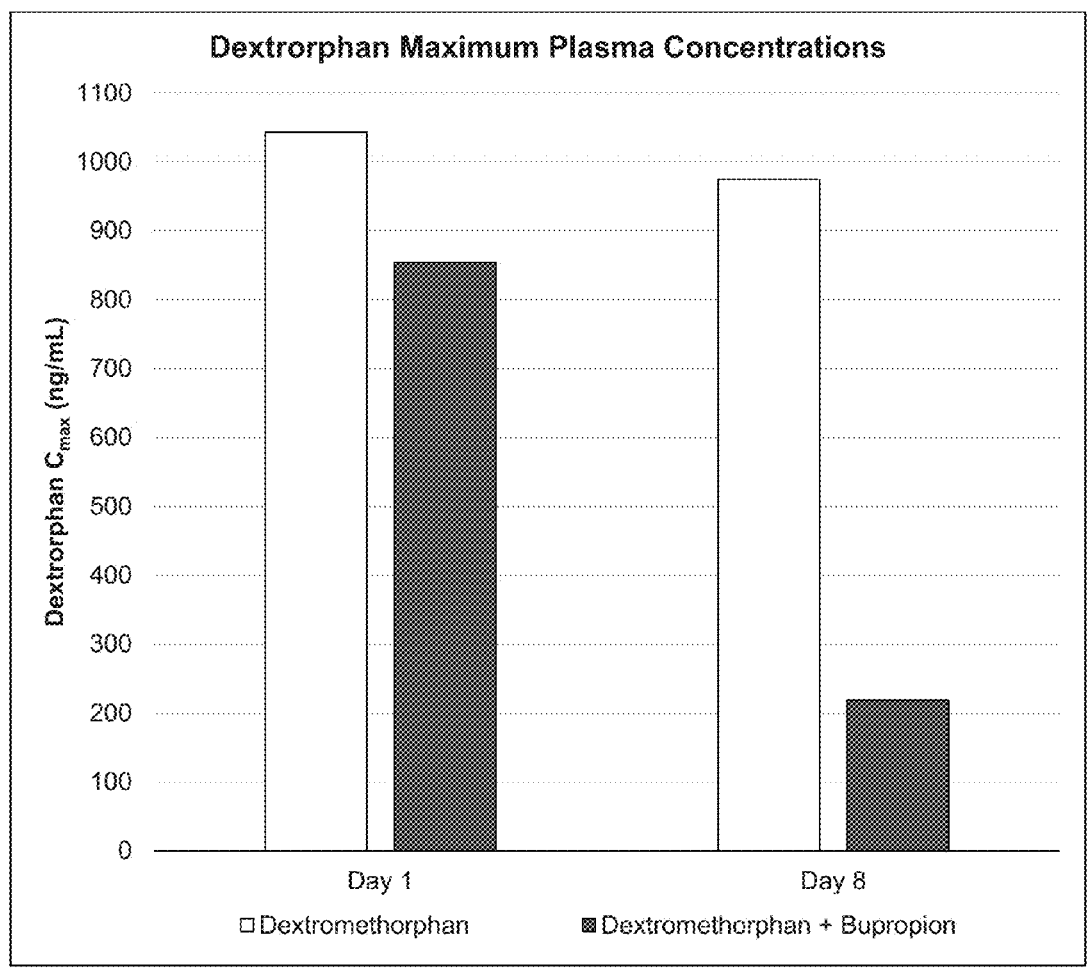
FIG. 10 depicts mean dextrorphan maximum plasma concentrations on Day 1 and Day 8 for subjects administered dextromethorphan alone or dextromethorphan and bupropion.
Figure 11:
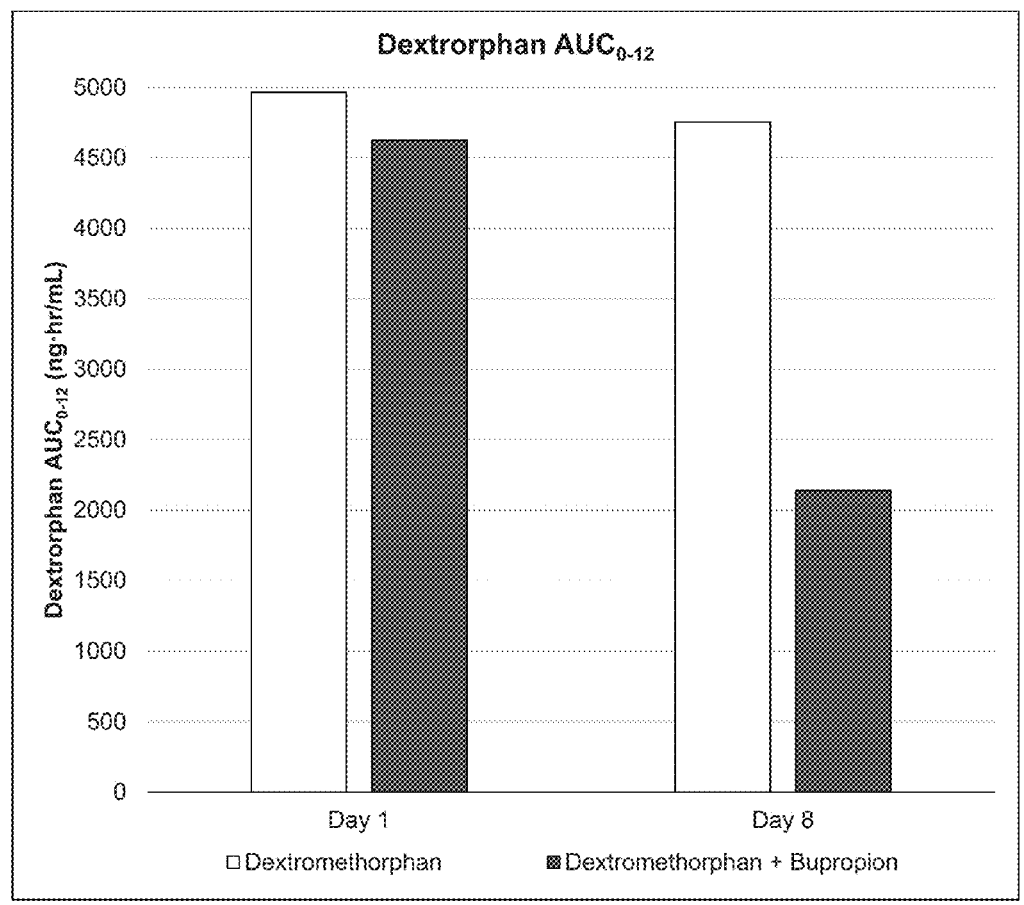
FIG. 11 depicts mean $AUC_{0-12}$ of dextrorphan on Day 1 and Day 8 for subjects administered dextromethorphan alone or dextromethorphan and bupropion.

As shown in FIGS. 10-11, there was an approximate 78% reduction in mean dextrorphan $C_{max}$, and an approximate 55% reduction in mean dextrorphan $AUC_{0-12}$ on Day 8 with administration of bupropion.

Phenotypic determination of dextromethorphan metabolizer status showed that no subjects in either treatment arm were poor metabolizers on Day 1. On Day 8 however, 100% of subjects treated with bupropion had converted to poor metabolizer status as compared to 0% of subjects treated with dextromethorphan alone. The mean plasma dextromethorphan/dextrorphan metabolic ratio increased from 0.01 on Day 1 to 0.71 on Day 8 with bupropion administration. The mean ratio in the group administered DM alone was 0.00 on Day 1 and remained unchanged on Day 8.

On Day 8, average plasma concentrations of bupropion, hydroxybupropion, erythrohydroxybupropion, and threohydroxybupropion were at least 10 ng/mL, 200 ng/mL, 20 ng/mL, and 100 ng/mL, respectively after bupropion administration.

As used in this section, the term "fold change" or "fold increase" refers to the ratio of a value for bupropion with dextromethorphan to the same value for dextromethorphan alone (i.e. the value for bupropion with dextromethorphan divided by the same value for dextromethorphan alone).

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of increasing dextromethorphan plasma levels in a human being that is an extensive metabolizer of dextromethorphan in need of treatment with dextromethorphan, comprising co-administering a) erythrohydroxybupropion or bupropion with b) dextromethorphan to the human being once or twice a day for at least eight consecutive days, wherein the daily dose of dextromethorphan is about 40 mg to about 600 mg, and co-administering erythrohydroxybupropion or bupropion with dextromethorphan results in an $AUC_{0-12}$ of dextromethorphan that, on the eighth day, is at least about 20 times the $AUC_{0-12}$ that would be achieved by administering the same amount of dextromethorphan without erythrohydroxybupropion or bupropion for eight consecutive days.

2. The method of claim 1, wherein the daily dose of dextromethorphan is about 60 mg to about 260 mg.

3. The method of claim 1, wherein the daily dose of dextromethorphan is about 60 mg to about 120 mg.

4. The method of claim 1, wherein the daily dose of dextromethorphan is about 40 mg to about 100 mg.

5. The method of claim 1, wherein dextromethorphan is co-administered in a dosage form that contains about 40 mg to about 50 mg of dextromethorphan.

6. The method of claim 4, wherein dextromethorphan is co-administered in a dosage form that contains about 40 mg to about 50 mg of dextromethorphan.

7. The method of claim 1, wherein erythrohydroxybupropion or bupropion and dextromethorphan are co-administered together in a single, solid oral dosage form.

8. The method of claim 7, wherein the single, solid oral dosage form further comprises a binder, a disintegrating agent, or a lubricant.

9. The method of claim 1, further comprising co-administering erythrohydroxybupropion or bupropion with dextromethorphan to the human being once or twice a day for at least 30 consecutive days.

10. The method of claim 1, further comprising co-administering erythrohydroxybupropion or bupropion with dextromethorphan to the human being once or twice a day for at least 60 consecutive days.

11. The method of claim 1, further comprising co-administering erythrohydroxybupropion or bupropion with dextromethorphan to the human being once or twice a day for at least 180 consecutive days.

12. The method of claim 1, comprising co-administering erythrohydroxybupropion or bupropion with dextromethorphan to the human being twice a day.

13. The method of claim 1, comprising co-administering erythrohydroxybupropion or bupropion with dextromethorphan to the human being once a day.

14. The method of claim 1, wherein, on the eighth day, the $AUC_{0-12}$ of erythrohydroxybupropion is at least about 200 ng·hr/mL.

15. The method of claim 1, wherein, on the eighth day, the $AUC_{0-12}$ of erythrohydroxybupropion is at least about 400 ng·hr/mL.

16. The method of claim 1, wherein erythrohydroxybupropion, bupropion, or dextromethorphan is deuterium-modified.

17. The method of claim 16, wherein dextromethorphan is deuterium-modified.

18. The method of claim 1, wherein erythrohydroxybupropion or bupropion and dextromethorphan are independently administered either orally or parenterally.

19. The method of claim 18, wherein erythrohydroxybupropion or bupropion and dextromethorphan are orally administered in a solid or liquid dosage form.

20. The method of claim 19, wherein the solid dosage form is a tablet, a troche, a pill, or a capsule.

21. The method of claim 20, wherein bupropion and dextromethorphan independently comprise at least 5% (w/w) of the solid dosage form.

22. The method of claim 19, wherein bupropion and dextromethorphan independently comprise at least 0.0001% (w/v) of the liquid dosage form.

23. The method of claim 8, wherein the binder comprises gum tragacanth, acacia, corn starch, or gelatin.

24. The method of claim 8, wherein the disintegrating agent comprises corn starch, potato starch, or alginic acid.

25. The method of claim 8, wherein the lubricant comprises magnesium stearate.

26. The method of claim 1, wherein erythrohydroxybupropion or bupropion and dextromethorphan are co-administered as two separate dosage forms.

27. The method of claim 18, wherein the liquid dosage form comprises a liquid or a solid phase dispersion.

* * * * *